(12) United States Patent
Couture et al.

(10) Patent No.: US 8,267,935 B2
(45) Date of Patent: Sep. 18, 2012

(54) ELECTROSURGICAL INSTRUMENT REDUCING CURRENT DENSITIES AT AN INSULATOR CONDUCTOR JUNCTION

(75) Inventors: Gary M. Couture, Longmont, CO (US); Robert M. Sharp, Boulder, CO (US); Craig Weinberg, Denver, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 1324 days.

(21) Appl. No.: 11/732,556

(22) Filed: Apr. 4, 2007

(65) Prior Publication Data
US 2008/0249527 A1    Oct. 9, 2008

(51) Int. Cl.
*A61B 18/14* (2006.01)
(52) U.S. Cl. .................................. 606/51; 606/52
(58) Field of Classification Search ............... 606/50–52
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,459,187 A | 3/1967 | Pallotta |
| 3,372,288 A | 3/1968 | Wigington |

(Continued)

FOREIGN PATENT DOCUMENTS

CA    2104423    2/1994

(Continued)

OTHER PUBLICATIONS

Int'l Search Report EP 06 020574.7 dated Sep. 21, 2007.

(Continued)

*Primary Examiner* — Michael Peffley
*Assistant Examiner* — Samantha Good

(57) ABSTRACT

An electrosurgical instrument having opposing end effectors and a handle for effecting movement of the end effectors relative to one another, includes a pair of electrodes each including an electrically conductive surface (e.g., which can be dimensioned for sealing, clamping and/or cutting), an insulating substrate having a first edge, and an insulating layer positioned in a channel formed by the electrically conductive surface within the first edge between the conductive surface and the first edge of the insulating substrate. The insulating layer has a portion proximal to the electrically conductive surface and a portion distal from the electrically conductive surface and a gradient such that the proximal portion has a lower dielectric strength than the distal portion. A coating on one of the pair of electrodes may be disposed in at least partial non-vertical registration with a coating on the opposing one of the pair of electrodes.

14 Claims, 14 Drawing Sheets

U.S. PATENT DOCUMENTS

| | | |
|---|---|---|
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |

| Patent No. | Date | Inventor |
|---|---|---|
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |

| Patent No. | Date | Inventor |
|---|---|---|
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |

| Patent No. | Kind | Date | Inventor(s) |
|---|---|---|---|
| 6,461,352 | B2 | 10/2002 | Morgan et al. |
| 6,461,368 | B2 | 10/2002 | Fogarty et al. |
| 6,464,701 | B1 | 10/2002 | Hooven et al. |
| 6,464,702 | B2 | 10/2002 | Schulze et al. |
| 6,464,704 | B2 | 10/2002 | Schmaltz et al. |
| 6,485,489 | B2 | 11/2002 | Teirstein et al. |
| 6,494,888 | B1 | 12/2002 | Laufer et al. |
| 6,500,176 | B1 | 12/2002 | Truckai et al. |
| 6,506,196 | B1 | 1/2003 | Laufer |
| 6,508,815 | B1 | 1/2003 | Strul et al. |
| 6,511,480 | B1 | 1/2003 | Tetzlaff et al. |
| 6,514,215 | B1 | 2/2003 | Ouchi |
| 6,514,252 | B2 | 2/2003 | Nezhat et al. |
| 6,517,539 | B1 | 2/2003 | Smith et al. |
| 6,527,771 | B1 | 3/2003 | Weadock et al. |
| 6,533,784 | B2 | 3/2003 | Truckai et al. |
| 6,545,239 | B2 | 4/2003 | Spedale et al. |
| 6,558,385 | B1 | 5/2003 | McClurken et al. |
| 6,562,037 | B2 | 5/2003 | Paton et al. |
| 6,569,105 | B1 | 5/2003 | Kortenbach et al. |
| 6,582,450 | B2 | 6/2003 | Ouchi |
| 6,585,735 | B1 | 7/2003 | Frazier et al. |
| 6,602,252 | B2 | 8/2003 | Mollenauer |
| 6,605,790 | B2 | 8/2003 | Yoshida |
| 6,616,658 | B2 | 9/2003 | Ineson |
| 6,616,661 | B2 | 9/2003 | Wellman et al. |
| 6,620,161 | B2 | 9/2003 | Schulze et al. |
| 6,620,184 | B2 | 9/2003 | De Laforcade et al. |
| 6,626,901 | B1 | 9/2003 | Treat et al. |
| 6,638,287 | B2 | 10/2003 | Danitz et al. |
| 6,641,595 | B1 | 11/2003 | Moran et al. |
| 6,652,514 | B2 | 11/2003 | Ellman et al. |
| 6,652,521 | B2 | 11/2003 | Schulze |
| 6,656,175 | B2 | 12/2003 | Francischelli et al. |
| 6,656,177 | B2 | 12/2003 | Truckai et al. |
| 6,660,072 | B2 | 12/2003 | Chatterjee |
| 6,663,639 | B1 | 12/2003 | Laufer et al. |
| 6,663,641 | B1 | 12/2003 | Kovac et al. |
| 6,666,854 | B1 | 12/2003 | Lange |
| 6,669,696 | B2 | 12/2003 | Bacher et al. |
| 6,673,092 | B1 | 1/2004 | Bacher |
| 6,676,660 | B2 | 1/2004 | Wampler et al. |
| 6,676,676 | B2 | 1/2004 | Danitz et al. |
| 6,679,882 | B1 | 1/2004 | Kornerup |
| 6,682,527 | B2 | 1/2004 | Strul |
| 6,682,528 | B2 | 1/2004 | Frazier et al. |
| 6,685,724 | B1 | 2/2004 | Haluck |
| 6,689,131 | B2 | 2/2004 | McClurken |
| 6,692,445 | B2 | 2/2004 | Roberts et al. |
| 6,693,246 | B1 | 2/2004 | Rudolph et al. |
| 6,695,840 | B2 | 2/2004 | Schulze |
| 6,702,810 | B2 | 3/2004 | McClurken et al. |
| 6,723,092 | B2 | 4/2004 | Brown et al. |
| 6,726,068 | B2 | 4/2004 | Miller |
| 6,726,686 | B2 | 4/2004 | Buysse et al. |
| 6,726,694 | B2 | 4/2004 | Blatter et al. |
| 6,733,498 | B2 | 5/2004 | Paton et al. |
| 6,736,813 | B2 | 5/2004 | Yamauchi et al. |
| 6,743,229 | B2 | 6/2004 | Buysse et al. |
| 6,743,230 | B2 | 6/2004 | Lutze et al. |
| 6,743,239 | B1 | 6/2004 | Kuehn et al. |
| 6,743,240 | B2 | 6/2004 | Smith et al. |
| 6,755,843 | B2 | 6/2004 | Chung et al. |
| 6,756,553 | B1 | 6/2004 | Yamaguchi et al. |
| 6,757,977 | B2 | 7/2004 | Dambal et al. |
| D493,888 | S | 8/2004 | Reschke |
| 6,770,072 | B1 | 8/2004 | Truckai et al. |
| 6,773,409 | B2 | 8/2004 | Truckai et al. |
| 6,773,432 | B1 | 8/2004 | Clayman et al. |
| 6,773,434 | B2 | 8/2004 | Ciarrocca |
| 6,773,441 | B1 | 8/2004 | Laufer et al. |
| 6,775,575 | B2 | 8/2004 | Bommannan et al. |
| 6,776,780 | B2 | 8/2004 | Mulier et al. |
| 6,786,905 | B2 | 9/2004 | Swanson et al. |
| 6,790,217 | B2 | 9/2004 | Schulze et al. |
| 6,796,981 | B2 | 9/2004 | Wham et al. |
| D496,997 | S | 10/2004 | Dycus et al. |
| 6,800,825 | B1 | 10/2004 | Sasaki et al. |
| 6,802,843 | B2 | 10/2004 | Truckai et al. |
| 6,808,525 | B2 | 10/2004 | Latterell et al. |
| D499,181 | S | 11/2004 | Dycus et al. |
| 6,818,000 | B2 | 11/2004 | Muller et al. |
| 6,821,285 | B2 | 11/2004 | Laufer et al. |
| 6,835,200 | B2 | 12/2004 | Laufer et al. |
| 6,857,357 | B2 | 2/2005 | Fujii |
| 6,860,880 | B2 | 3/2005 | Treat et al. |
| 6,887,240 | B1 | 5/2005 | Lands et al. |
| 6,889,116 | B2 | 5/2005 | Jinno |
| 6,914,201 | B2 | 7/2005 | Van Vooren et al. |
| 6,926,716 | B2 | 8/2005 | Baker et al. |
| 6,929,644 | B2 | 8/2005 | Truckai et al. |
| 6,932,810 | B2 | 8/2005 | Ryan |
| 6,932,816 | B2 | 8/2005 | Phan |
| 6,934,134 | B2 | 8/2005 | Mori et al. |
| 6,936,061 | B2 | 8/2005 | Sasaki |
| D509,297 | S | 9/2005 | Wells |
| 6,942,662 | B2 | 9/2005 | Goble et al. |
| 6,943,311 | B2 | 9/2005 | Miyako |
| 6,953,430 | B2 | 10/2005 | Kidooka |
| 6,953,461 | B2 | 10/2005 | McClurken et al. |
| 6,958,070 | B2 | 10/2005 | Witt et al. |
| 6,960,210 | B2 | 11/2005 | Lands et al. |
| 6,964,662 | B2 | 11/2005 | Kidooka |
| 6,966,907 | B2 | 11/2005 | Goble |
| 6,972,017 | B2 | 12/2005 | Smith et al. |
| 6,977,495 | B2 | 12/2005 | Donofrio |
| 6,979,786 | B2 | 12/2005 | Aukland et al. |
| 6,981,628 | B2 | 1/2006 | Wales |
| 6,987,244 | B2 | 1/2006 | Bauer |
| 6,994,707 | B2 | 2/2006 | Ellman et al. |
| 6,994,709 | B2 | 2/2006 | Iida |
| 6,997,931 | B2 | 2/2006 | Sauer et al. |
| 7,001,381 | B2 | 2/2006 | Harano et al. |
| 7,011,657 | B2 | 3/2006 | Truckai et al. |
| 7,033,354 | B2 | 4/2006 | Keppel |
| 7,033,356 | B2 | 4/2006 | Latterell et al. |
| 7,041,102 | B2 | 5/2006 | Truckai et al. |
| 7,044,948 | B2 | 5/2006 | Keppel |
| 7,052,489 | B2 | 5/2006 | Griego et al. |
| 7,052,496 | B2 | 5/2006 | Yamauchi |
| 7,063,715 | B2 | 6/2006 | Onuki et al. |
| D525,361 | S | 7/2006 | Hushka |
| 7,070,597 | B2 | 7/2006 | Truckai et al. |
| 7,083,618 | B2 | 8/2006 | Couture et al. |
| 7,083,619 | B2 | 8/2006 | Truckai et al. |
| 7,083,620 | B2 | 8/2006 | Jahns et al. |
| 7,087,051 | B2 | 8/2006 | Bourne et al. |
| 7,087,054 | B2 | 8/2006 | Truckai et al. |
| 7,090,673 | B2 | 8/2006 | Dycus et al. |
| 7,090,689 | B2 | 8/2006 | Nagase et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,103,947 | B2 | 9/2006 | Sartor et al. |
| 7,107,124 | B2 | 9/2006 | Green |
| 7,112,199 | B2 | 9/2006 | Cosmescu |
| D531,311 | S | 10/2006 | Guerra et al. |
| 7,115,123 | B2 | 10/2006 | Knowlton et al. |
| 7,118,570 | B2 | 10/2006 | Tetzlaff et al. |
| 7,118,587 | B2 | 10/2006 | Dycus et al. |
| 7,131,860 | B2 | 11/2006 | Sartor et al. |
| 7,131,970 | B2 | 11/2006 | Moses et al. |
| 7,131,971 | B2 | 11/2006 | Dycus et al. |
| 7,135,020 | B2 | 11/2006 | Lawes et al. |
| 533,942 | A1 | 12/2006 | Kerr et al. |
| 7,145,757 | B2 | 12/2006 | Shea et al. |
| 7,147,638 | B2 | 12/2006 | Chapman et al. |
| 7,150,097 | B2 | 12/2006 | Sremcich et al. |
| 7,150,749 | B2 | 12/2006 | Dycus et al. |
| 7,153,314 | B2 | 12/2006 | Laufer et al. |
| D535,027 | S | 1/2007 | James et al. |
| 7,156,842 | B2 | 1/2007 | Sartor et al. |
| 7,156,846 | B2 | 1/2007 | Dycus et al. |
| 7,160,298 | B2 | 1/2007 | Lawes et al. |
| 7,160,299 | B2 | 1/2007 | Baily |
| 7,169,146 | B2 | 1/2007 | Truckai et al. |
| 7,179,255 | B2 | 2/2007 | Lettice et al. |
| 7,179,258 | B2 | 2/2007 | Buysse et al. |

| | | |
|---|---|---|
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |

| | | |
|---|---|---|
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0077131 A1* | 3/2008 | Yates et al. ...................... 606/48 |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 0853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |

| | | |
|---|---|---|
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3.dated Jan. 16, 2008.
International Search Report EP08006732.5-2305 Dated: Jul. 29, 2008.
Sampayan Se et al., "Multilayer Ultra-High Gradient Insulator Technology" Discharges and Electrical Insulation in Vacuum, 1998. Proceedings ISDE IV. XVIIITH International Symposium on Eindhoven, Netherlands Aug. 17-21, 1998, New York, NY, US, IEEE, US.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo at al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Seating Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, ☐Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, ☐Jun. 2003.

Craig Johnson, "Use of the LigaSure Vessel Sealing System in Bloodless Hemorrhoidectomy" Innovations That Work, ☐Mar. 2000.

Muller et al., "Extended Left Hemicolectomy Using the LigaSure Vessel Sealing System" Innovations That Work,☐Sep. 1999.

Herman et al., "Laparoscopic Intestinal Resection With the LigaSure Vessel Sealing System: A Case Report" Innovations That Work,☐Feb. 2002.

Carus et al., "Initial Experience With The LigaSure Vessel Sealing System in Abdominal Surgery" Innovations That Work,☐Jun. 2002.

Levy et al, "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
European Search Report No. 10186527.7 dated Jun. 17, 2011.

* cited by examiner

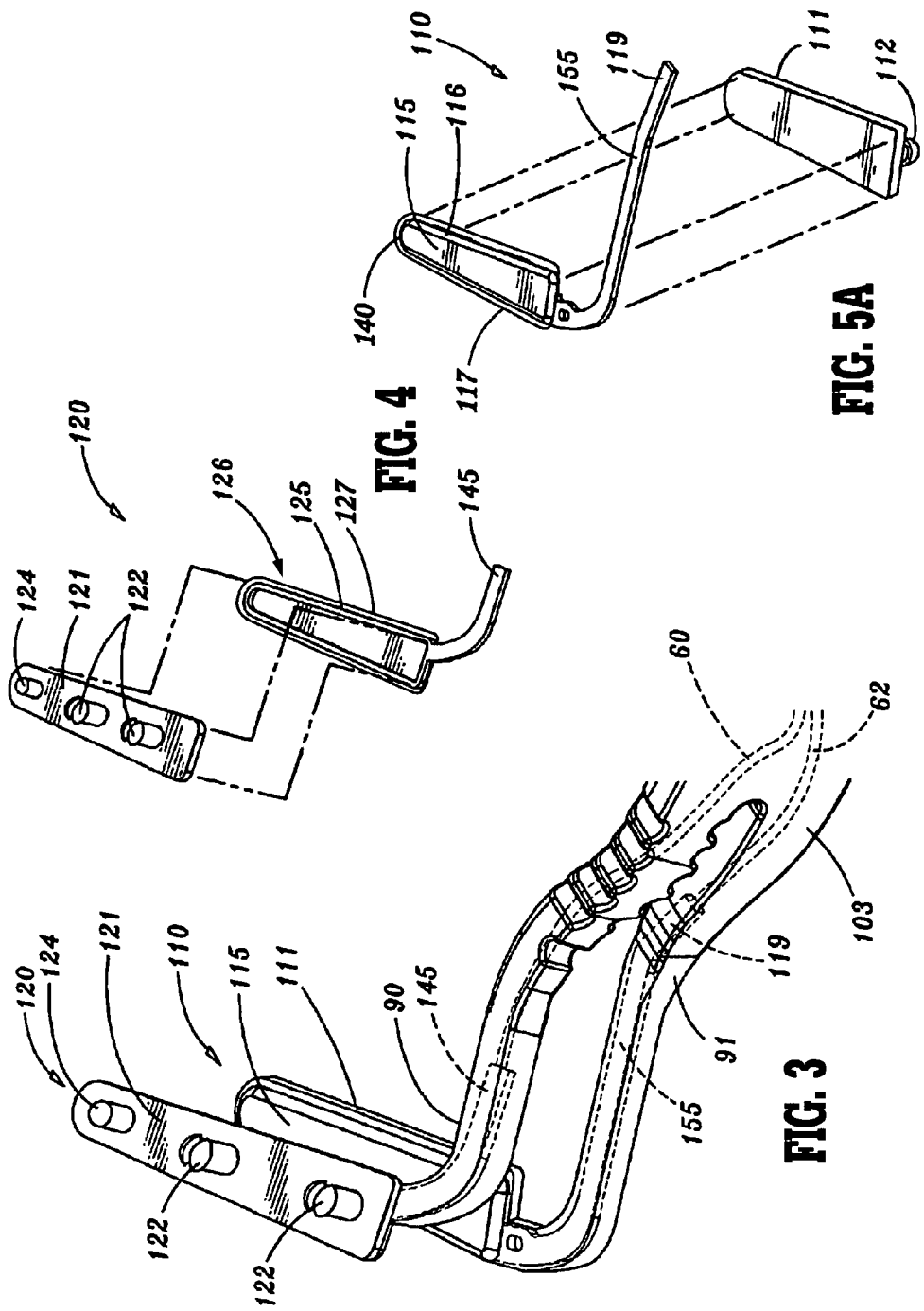

ELECTROSURGICAL INSTRUMENT REDUCING CURRENT DENSITIES AT AN INSULATOR CONDUCTOR JUNCTION

BACKGROUND

1. Technical Field

The present disclosure relates to electrosurgical instruments used for open and endoscopic surgical procedures. More particularly, the present disclosure relates to electrosurgical instruments having an electrode assembly which is designed to disperse or minimize energy concentrations and/or current densities that occur at the junction between insulating material and a conductor, reduce the incidence of flashover during activation and limit thermal spread to adjacent tissue structures.

2. Background

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate tissue and/or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are generally disposed on the inner facing or opposing surfaces of the end effectors which are, in turn, electrically coupled to an electrosurgical generator. Each electrode is charged to a different electric potential. Since tissue is a conductor of electrical energy, when the end effectors are utilized to clamp, grasp, seal and/or cut tissue therebetween, the electrical energy can be selectively transferred through the tissue.

It is known that the process of coagulating small vessels is fundamentally different than vessel sealing. For the purposes herein the term "coagulation" is defined as a process of desiccating tissue wherein the tissue cells are ruptured and dried. The term "vessel sealing" is defined as the process of liquefying the collagen in the tissue so that the tissue cross-links and reforms into a fused mass. Thus, coagulation of small vessels is sufficient to close them, however, larger vessels need to be sealed to assure permanent closure.

With particular respect to vessel sealing, in order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Using electrosurgical instruments to seal, cut and/or cauterize tissue may result in some degree of so-called "thermal spread" across adjacent tissue structure. For the purposes herein, the term "thermal spread" refers generally to the heat transfer (heat conduction, heat convection or electrical current dissipation) traveling along the periphery of the electrically conductive surfaces. This can also be termed "collateral damage" to adjacent tissue. As can be appreciated, reducing the thermal spread during an electrical procedure reduces the likelihood of unintentional or undesirable collateral damage to surrounding tissue structures which are adjacent to an intended treatment site.

Instruments which include dielectric coatings disposed along the outer surfaces are known and are used to prevent tissue "blanching" at points normal to the activation site. In other words, these coatings are primarily designed to reduce accidental burning of tissue as a result of incidental contact with the outer surfaces end effectors. So far as is known these coating are not designed or intended to reduce collateral tissue damage or thermal spread to adjacent tissue (tissue lying along the tissue plane). Moreover, such coatings are not designed or intended to reduce or displace energy concentrations that can occur at the junction of an insulating material and an active conductor.

Cleaning and sterilizing many of the prior art bipolar instruments is often impractical as electrodes and/or insulation can be damaged. More particularly, electrically insulative materials, such as plastics, can be damaged or compromised by repeated sterilization cycles which may ultimately effect the reliability of the instrument and cause so-called "flashover." Flashover as used herein relates to a visual anomaly which develops as a result of inconsistent current tracking over the surface of the insulator or insulative coating and/or activation irregularities which may occur when the instrument is repeatedly used during surgery. Put simply, flashover tends to char the surface of the insulate and may effect the life of the instrument and/or the electrode assembly. The effects and industry standards with respect to flashover are discussed in detail in the Annual Book of ASTM Standards, Vol. 10.02, Designations: D495-84; D618; D2303; and D3638.

Firing many of the prior art bipolar instruments is problematic in that energy concentrations and/or heat can be formed at or near the junction between the insulator and an adjacent conductive surface. The energy concentrations may promote inconsistent current trackings or activation irregularities during surgery. Moreover, during repeated use of the instrument, heat can damage or compromise the insulative material of the instrument.

SUMMARY

The present disclosure relates generally to an open and/or endoscopic electrosurgical instrument which includes opposing end effectors and a handle for effecting movement of the end effectors relative to one another. The instrument generally includes housing, and a pair of electrodes. Each electrode may include an electrically conductive surface, an insulating substrate having a top edge, and an insulating layer having a top portion and a bottom portion. The insulating layer may be positioned between the conductive surface and the top edge of the insulating substrate. The insulating layer may have a gradient such that the top portion has a lower dielectric strength than the bottom portion. The uniquely-designed configuration of the insulating substrate in connection with the insulating layer and chemical characteristics of the insulating layer also contributes to a reduction in the incidence of flashover, and current concentration buildup.

More particularly, the present disclosure relates to an open and/or endoscopic electrosurgical instrument which includes an insulating layer that is a gradient insulating layer where the top portion has lower dielectric strength than the bottom portion. In some embodiments, the insulating layer may have varying dielectric strengths between the top portion and the bottom portion. Optionally, the top portion of the insulating layer may be less insulating than the bottom portion. In particular embodiments, the insulating layer may have at least one middle portion between the top portion of the gradient layer and the bottom portion of the gradient layer, such as one or more middle portions including a plurality of middle portions with various dielectric strengths. For example, one or more middle portions may have a higher dielectric strength than the top portion of the gradient layer, and a lower dielectric strength than the bottom portion of the gradient layer. Thus, in embodiments, the dielectric strength of the top portion of the insulating layer may be different from the dielectric strength of the bottom portion of the insulating layer to reduce energy concentrations between the top edge of the insulating substrate and the electrically conductive surface.

In other embodiments, the present disclosure relates to an electrosurgical instrument having opposing end effectors and a handle for effecting movement of the end effectors relative to one another. The electrosurgical instrument has a pair of electrodes each including an electrically conductive surface and an insulating substrate having a first edge. An insulating layer is positioned in a channel formed by the conductive surface and the first edge of the insulating substrate. The insulating layer has a portion proximal to the electrically conductive surface and a portion distal from the electrically conductive surface and a gradient such that the proximal portion has a lower dielectric strength than the distal portion.

In some embodiments, the insulating layer may be made of material such as ceramic, polymer, thermoplastic, semi-conductive material, and combinations of these materials. For example, the insulating layer may be made of ABS, acetate, acrylic, beryllium oxide, ceramic, delrin, epoxy, fiberglass, glass, kapton, kynar, lexan, melron, melamine, mica, neoprene, nomex, nylon, polyethylene terephthalate, PETG, phenolics, polyester, polyolefin, polyurethane, PVC, silicone, silicone rubber, TEFLON, thermoplastic, electrical insulating papers, tape, foam, neoprene, polystyrene, polyurethane, vinyl, laminate, and/or combinations of these materials. Furthermore, the insulating layer may be made of semiconductive polymer. Moreover, the insulating layer may be made of conductive composites, conductive polymers, metal, carbon black, and/combinations of these materials.

The insulating layer may be mounted to the electrically conductive surface by various methods including a thermally sprayed process, a vacuum deposition process, a powder coating process, overmolding a stamped plate, and/or combinations of these processes.

In some embodiments, the electrically conductive surfaces are offset in relation to one another.

In some embodiments, the electrically conductive surfaces of the opposing jaw members cooperate to seal tissue.

The present disclosure further relates to an electrosurgical instrument having a handle and at least one shaft for effecting movement of a pair of opposing end effectors relative to one another. The instrument includes a housing, a first electrode having a first electrically conductive surface having a first geometric shape and a first insulating substrate having a second geometric shape, and a first insulating gradient layer disposed between the first conductive surface and the first insulating substrate. The first electrode may be integrally associated with the end effector of the instrument. The instrument may further include a second electrode having a second electrically conductive surface having a second geometric shape and a second insulating substrate having a second geometric shape, and a second insulating gradient layer disposed between the second conductive surface and the second insulating substrate. The second electrode may be integrally associated with the end effector of the instrument such that the second electrode resides in opposing relation relative to the first electrode. In particular embodiments, the first conductive surface and the second conductive surface are offset in relation to one another.

The present disclosure also relates to an electrosurgical instrument having opposing end effectors and a handle for effecting movement of the end effectors relative to one another. The electrosurgical instrument also includes a pair of symmetrically disposed opposing electrodes each having an electrically conductive surface. An insulating substrate is also included having an exterior surface, which intersects the electrically conductive surface to form at least one insulator-conductor junction point therebetween. A coating is disposed in proximity to the insulator-conductor junction point(s). The coating on one of the pair of electrodes is disposed in at least partial non-vertical registration with the coating on the opposing electrode.

The present disclosure also relates to an electrosurgical instrument having opposing end effectors and a handle for effecting movement of the end effectors relative to one another. The electrosurgical instrument also includes a pair of opposing electrodes each having an electrically conductive surface and an insulating substrate having an exterior surface. The exterior surface of the insulating substrate intersects the electrically conductive surface to form at least one insulator-conductor junction point therebetween. The electrically conductive surface of one of the pair of opposing electrodes is disposed in at least partial non-vertical registration with the electrically conductive surface on the opposing electrode.

In one embodiment, the electrically conductive surface of one of the pair of opposing electrodes includes a cross-sectional width dimension that is greater than a cross-sectional width dimension of the other of the pair of opposing electrodes.

In another embodiment, the electrosurgical instrument includes a coating disposed in proximity to the at least one insulator-conductor junction point which provides a dielectric gradient such that a portion of the coating in closest proximity to the exterior surface of the insulating substrate has a dielectric strength that is greater than the dielectric strength of a portion of the coating in closest proximity to the electrically conductive surface.

These and other aspects of this disclosure will be evident upon reference to the following detailed description.

BRIEF DESCRIPTION OF THE DRAWINGS

FIG. 3 is an enlarged, perspective view of a distal end of the electrode assembly of FIG. 2;

FIG. 4 is a perspective view with parts separated of an upper electrode of the electrode assembly of FIG. 3;

FIG. 5A is a perspective view with parts separated of a lower electrode of the electrode assembly of FIG. 3;

DETAILED DESCRIPTION

Figure 1:
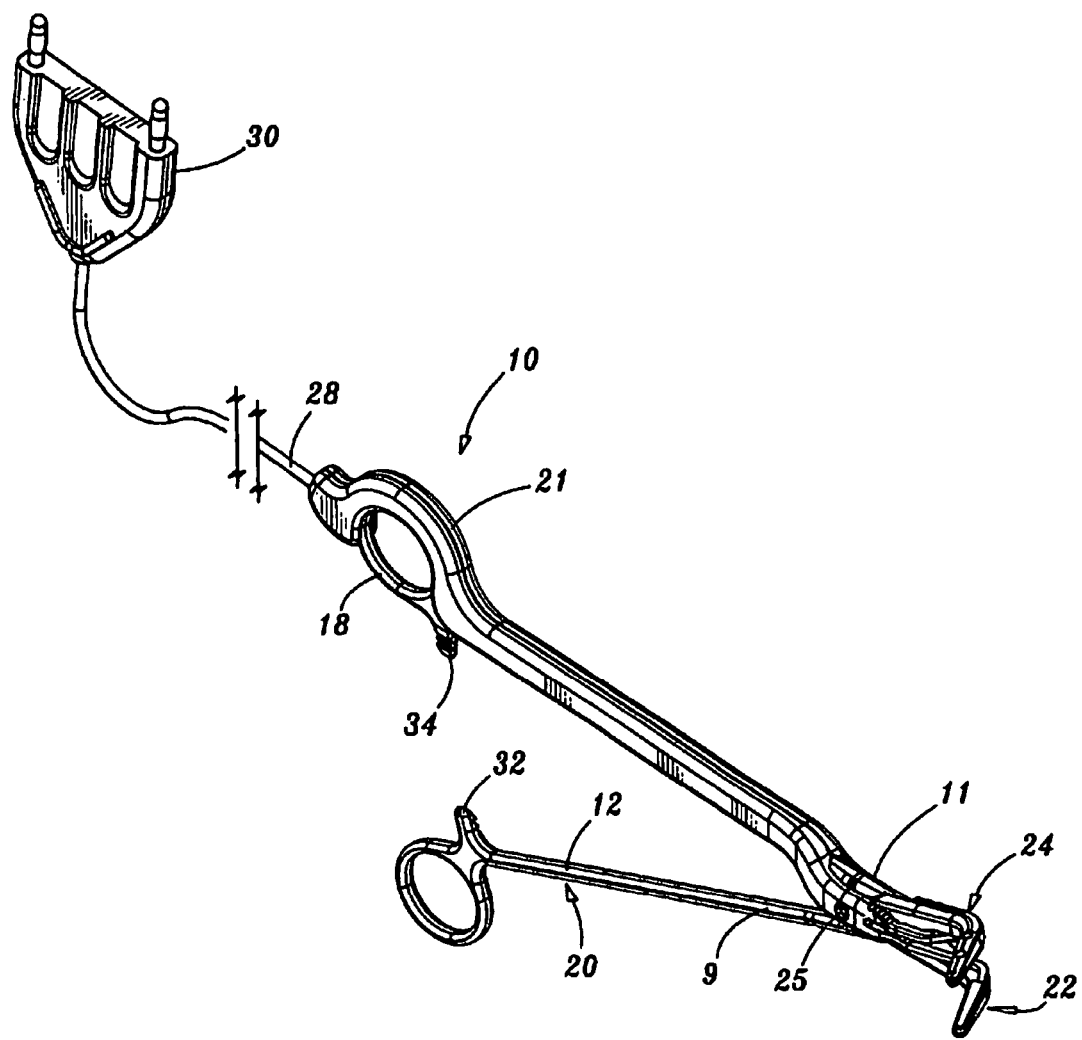
FIG. 1 is a perspective view of an open electrosurgical instrument according to one embodiment of the present disclosure.

It has been found that by providing an insulating layer between the junction of electrode insulating material and the electrically conductive surface, surgeons can more readily, more easily and more effectively reduce the incidence of current concentrations forming near the junctions, reduce the incidence of flashover, and/or reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue. The term "flashover" is simply a visual anomaly which occurs during activation as a result of inconsistent and/or irregular current tracking over the surface of the insulate which may occur when the instrument is repeatably used during surgery. Flashover tends to char the surfaces of the insulate and/or insulating layer and may affect the life of the instrument.

It is envisioned that the configuration of an insulating layer between conductive surface and the insulating material which surrounds the perimeter of the electrically conductive surface will effectively reduce stray currents forming at the junction. Moreover, the configuration will effectively reduce current and thermal dissipation to adjacent tissue areas and generally restrict current travel to areas between the opposing electrodes. As mentioned above, this is different from dielectrically coating the outer surfaces of the instrument to prevent tissue "blanching" at points normal to the intended site. These coatings are not designed or intended to reduce collateral tissue damage or thermal spread to adjacent tissue (tissue lying along the tissue activation plane).

More particularly, it is contemplated that altering the junction between a conductive electrode and its insulating material by providing an insulating layer therebetween alters the electrical path thereby influencing the thermal spread/collateral damage to adjacent tissue structures, as well as stray current concentrations formed at the junction. The insulating layer further isolates the two electrically opposing poles (i.e., electrodes) from one another thereby reducing the possibility that tissue or tissue fluids can create an unintended bridge or path for current travel. In other words, the insulator, insulating layer, and electrically conductive surface may be dimensioned such that the current is concentrated between the opposing electrically conductive surfaces as explained in more detail below.

It is also contemplated that one way to reduce the incidence of stray currents and flashover is to provide a gradient insulating layer between the insulating substrate, and the electrically conductive surface which effectively increases the overall distance that the electrical current must travel along the predetermined electrical path. As used herein the term "gradient" refers to a gradual change in some quantitative property over a specific distance. It is envisioned that the quantitative property of the gradient insulating layer is the dielectric strength of the at least one material of the gradient insulating layer. As used herein the term "dielectric strength" generally refers to a measure of electrical strength of a material such as an insulator. For example, dielectric strength may refer to the maximum voltage required to produce a dielectric breakdown through the material and is expressed as Volts per unit thickness. Generally, the higher the dielectric strength of a material the better its quality as an insulator. In some embodiments, the insulating layer may be a gradient insulating layer where the top portion of the gradient layer has lower dielectric strength than the bottom portion of the gradient layer. However, it is envisioned that the insulating layer may have varying dielectric strengths between the top portion thereof and the bottom portion. Moreover, the top portion of the insulating layer, or the portion that is adjacent the conductive plate, may be less insulating than the bottom portion of the gradient layer, or portion of the insulating layer that is adjacent to the insulating substrate. These configurations of the insulating layer are further described below.

It is also envisioned that manufacturing the insulating layer from a specific material having certain properties will, likewise, reduce the incidence of both current concentration near the junction of the insulating substrate and conductive surface, as well as flashover during activation. It is envisioned that the insulating layer may be made of semi-conductive material, conductive material, insulating material, or combinations of these materials. Non-limiting examples of suitable semi-conductive material includes semi-conductive polymers. Non-limiting examples of suitable conductive materials for use in accordance with the present disclosure include conductive composites, conductive polymers, metal, carbon black, and/or combinations thereof. Non-limiting examples of insulating materials suitable for use in accordance with the present disclosure include ABS, acetate, acrylic, beryllium oxide, ceramic, delrin, epoxy, fiberglass, glass, kapton, kynar, lexan, melron, melamine, mica, neoprene, nomex, nylon, polyethylene terephthalate, PETG, phenolics, polyester, polyolefin, polyurethane, PVC, silicone, silicone rubber, TEFLON, thermoplastic, electrical insulating papers, tape, foam, neoprene, polystyrene, polyurethane, vinyl, laminate, and/or combinations thereof. It is further envisioned that the insulating layer in accordance with the present disclosure may be made out of ceramic, polymer, thermoplastic, semi-conductive material, and combinations of these materials.

It is also envisioned that manufacturing the insulating layer by various steps will, likewise, reduce the incidence of both current concentration near the junction of the insulating substrate and conductive surface, as well as flashover during activation. Accordingly, the insulating layer may be mounted to the electrically conductive surface by overmolding a stamped plate; mounted to the electrically conductive surface by thermally sprayed process; mounted to the electrically conductive surface by a vacuum deposition process and/or mounted to the electrically conductive surface by a powder coating process.

Figure 2:
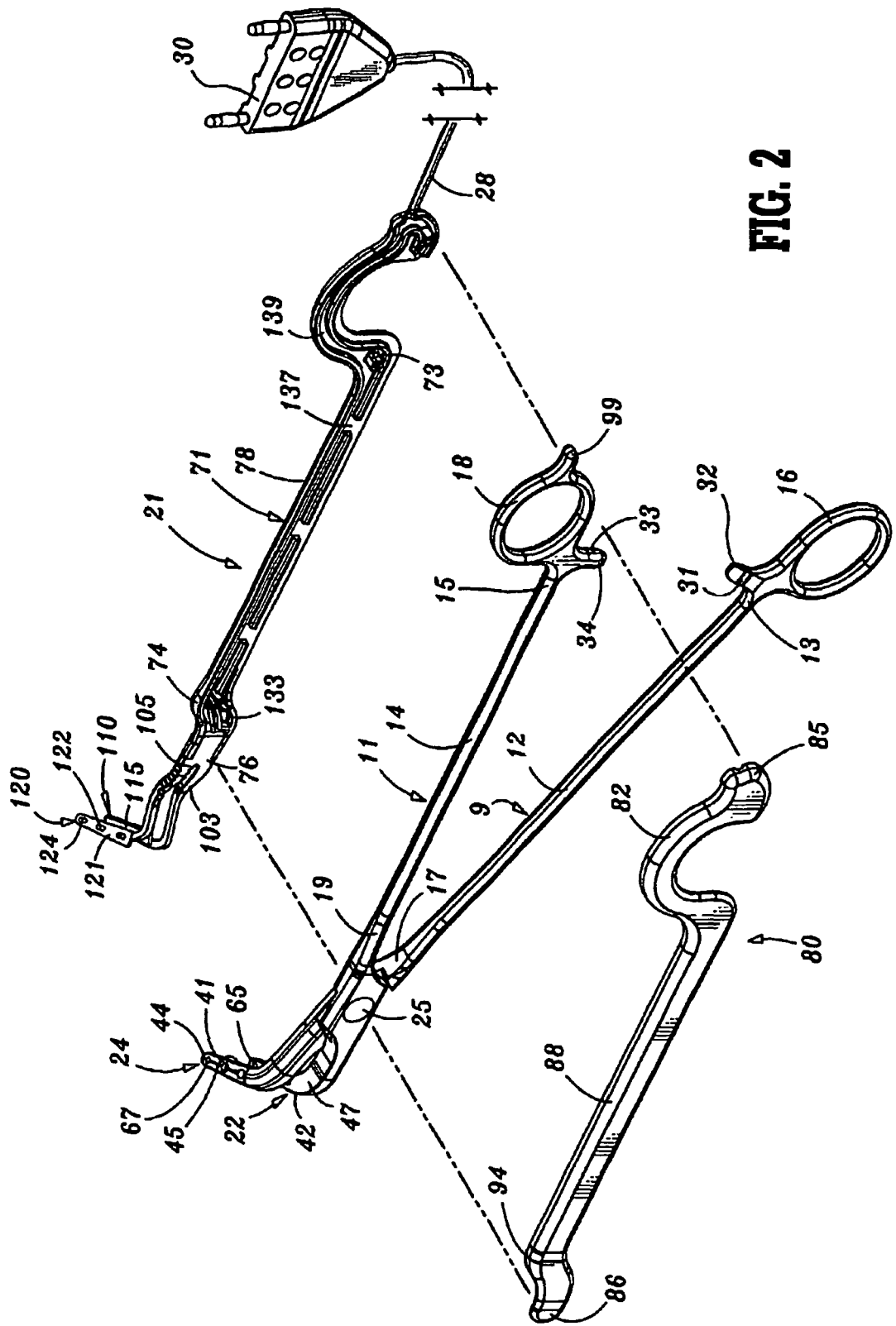
FIG. 2 is a perspective view with parts separated of the electrosurgical instrument shown in FIG. 1.

Referring now to FIGS. 1-2, a bipolar forceps 10 for use with open surgical procedures is shown by way of example and includes a mechanical forceps 20 and an electrode assembly 21. In the drawings and in the description which follows, the term "proximal", as is traditional, will refer to the end of the forceps 10 which is closer to the user, while the term "distal" will refer to the end which is further from the user. In addition, although the majority of the figures, i.e., FIGS. 1-5A and 6A, show embodiments of the presently described instrument for use with open surgical procedures, e.g., forceps 20, it is envisioned that the same properties as shown and described herein may also be employed with or incorporated on an endoscopic instrument 100 such as the embodiment shown by way of example in FIG. 6B.

FIGS. 1-2 show mechanical forceps 20 which includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto which allows a user to effect movement of at least one of the shaft portions, e.g., 12 relative to the other, e.g. 14. Extending from the distal ends 17 and 19 of each shaft portion 12 and 14 are end effectors 24 and 22, respectively. The end effectors 22 and 24 are movable relative to one another in response to movement of handle members 16 and 18.

In one embodiment, shaft portions 12 and 14 are affixed to one another at a point proximate the end effectors 24 and 22 about a pivot 25 such that movement of one of the handles 16, 18 will impart relative movement of the end effectors 24 and 22 from an open position wherein the end effectors 22 and 24 are disposed in spaced relation relative to one another to a closed position wherein the end effectors 22 and 24 incorporate a tubular vessel 150 therebetween (see FIGS. 6A and 6B) to effect sealing, cutting or grasping. It is envisioned that pivot 25 has a large surface area to resist twisting and movement of forceps 10 during activation. It is also envisioned that the forceps 10 can be designed such that movement of one or both of the handles 16 and 18 will only cause one of the end effectors, e.g., 24, to move with respect to the other end effector, e.g., 22.

As best seen in FIG. 2, end effector 24 includes an upper or first jaw member 44 which has an inner facing surface 45 and a plurality of mechanical interfaces disposed thereon which are dimensioned to releasable engage a portion of the electrode assembly 21 which will be described in greater detail below. Mechanical interfaces include sockets 41 disposed at least partially through inner facing surface 45 of jaw member 44 and dimensioned to receive a complementary detent 122 attached to upper electrode 120 of the disposable electrode assembly 21. While the term "socket" is used herein, it is contemplated that either a male or female mechanical interface may be used on jaw member 44 with a mating mechanical interface disposed on the electrode assembly 21.

In some cases, mechanical interfaces 41 may be manufactured along another side of jaw member 44 to engage a complementary mechanical interface of the electrode assembly 21 in a different manner, e.g., from the side. Jaw member 44 also includes an aperture 67 disposed at least partially through inner face 45 of end effector 24 which is dimensioned to receive a complementary guide pin 124 disposed on electrode 120 of the electrode assembly 21.

End effector 22 includes a second or lower jaw member 42 which has an inner facing surface 47 which opposes inner facing surface 45. In one embodiment, jaw members 42 and 44 are dimensioned generally symmetrically. However, in some cases, the two jaw members 42 and 44 may be manufactured asymmetrically depending upon a particular purpose. In much the same fashion as described above with respect to jaw member 44, jaw member 42 also includes a plurality of mechanical interfaces or sockets disposed thereon which are dimensioned to releasable engage a complementary portion 112 disposed on electrode 110 of the electrode assembly 21 as described below. Likewise, jaw member 42 also includes an aperture 65 disposed at least partially through inner face 47 which is dimensioned to receive a complementary guide pin disposed on electrode 110 of the electrode assembly 21.

End effectors 22, 24 (and, in turn, the jaw members 42 and 44 and the corresponding electrodes 110 and 120) are disposed at an angle alpha ($\alpha$) relative to the distal ends 19, 17. It is envisioned that angling the end effectors 22, 24 at an angle alpha ($\alpha$) relative to the distal ends 19, 17 may be advantageous for two reasons: 1) the angle of the end effectors, jaw members and electrodes will apply more constant pressure for cutting and/or for a constant tissue thickness at parallel for sealing purposes; and 2) the thicker proximal portion of the electrode, e.g., 110, (as a result of the taper along width "W") will resist bending due to the reaction force of the tissue 150. The tapered "W" shape of the electrode 110 is determined by calculating the mechanical advantage variation from the distal to proximal end of the electrode 110 and adjusting the width of the electrode 110 accordingly. Such end effectors suitable for use in accordance with the present disclosure are further shown and described in U.S. application Ser. No. 10/474,273 entitled Electrosurgical Instrument Reducing Thermal Spread to Lawes et al., herein incorporated by reference in its entirety.

Shaft members 12 and 14 of the mechanical forceps 20 are designed to transmit a particular desired force to the opposing inner facing surfaces of the jaw members 22 and 24, respectively, when clamped or during sealing and/or cutting. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34, respectively. Each ratchet, e.g., 32, extends from the proximal end 13 of its respective shaft member 12 towards the other ratchet 34 in a generally vertically-aligned manner such that the inner-facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. In one embodiment, each ratchet position holds a specific, i.e., constant, strain energy in the shaft members 12 and 14 which, in turn, transmits a specific force to the end effectors 22 and 24 and, thus, the electrodes 120 and 110. This is particularly relevant during sealing.

At least one of the shaft members, e.g., 14 may include a tang 99 which facilitates manipulation of the forceps 20 during surgical conditions as well as facilitates attachment of electrode assembly 21 on mechanical forceps 20 as will be described in greater detail below.

As best seen with respect to FIGS. 2-5A, the distal end 76 of electrode assembly 21 is bifurcated such that two prong-like members 103 and 105 extend outwardly therefrom to support electrodes 110 and 120, respectively. More particularly, electrode 120 is affixed at an end 90 of prong 105 and electrode 110 is affixed at an end 91 of prong 103. Electrodes 110 and 120 can be affixed to the ends 91 and 90 in any known manner, e.g., friction-fit, slide-fit, snap-fit engagement, crimping, etc. Moreover, it is contemplated that the electrodes 110 and 120 may be selectively removable from ends 90 and 91 depending upon a particular purpose and/or to facilitate assembly of the electrode assembly 21. As mentioned above, the inventive concepts disclosed herein may also relate to an electrosurgical instrument which does not include a selectively detachable electrode assembly, but, rather, includes end effectors which have integrally associated electrodes disposed thereon.

A pair of wires 60 and 62 are connected to the electrodes 120 and 110, respectively, as best seen in FIG. 3. Wires 60 and 62 are typically bundled together and form a wire bundle 28 (FIG. 2) which runs from a terminal connector 30 (see FIG. 2), to the proximal end of housing 71, along the interior of housing 71, to distal end 76. Wire bundle 28 is separated into wires 60 and 62 proximate distal end 76 and the wires 60 and 62 are connected to each electrode 120 and 110, respectively. In some cases, the wires 60 and 62 or the wire bundle 28 may be captured at various pinch points along the inner cavity of the electrode assembly 21 and enclose the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases, the wires 60 and 62 may be extended to an electrosurgical generator (not shown).

As best seen in FIG. 4, electrode 120 includes an electrically conductive surface 126, and an electrically insulative substrate 121 which are attached to one another by snap-fit engagement or some other method of assembly, e.g., slide-fit, overmolding of a stamping or metal injection molding. Disposed upon the outer edge of face 125 of electrically conductive surface 126 is insulating layer 127. Insulating layer 127 is made from semi-conductive material, conductive material, insulating material, or combinations of these materials. Non-limiting examples of suitable materials includes semi-conductive polymers, conductive composites, conductive polymers, metal, carbon black, ABS, acetate, acrylic, beryllium oxide, ceramic, delrin, epoxy, fiberglass, glass, kapton, kynar, lexan, melron, melamine, mica, neoprene, nomex, nylon, polyethylene terephthalate, PETG, phenolics, polyester, polyolefin, polyurethane, PVC, silicone, silicone rubber, TEFLON, thermoplastic, electrical insulating papers, tape, foam, neoprene, polystyrene, polyurethane, vinyl, laminate, and/or combinations thereof. It is further envisioned that the insulating layer 127 may be made out of ceramic, polymer, thermoplastic, semi-conductive material, and combinations of these materials. Insulating layer 127 is shaped to fit between the junction of substrate 121 and conductive surface 126 formed when these components are combined. The insulating layer 127 not only eliminates or reduces stray currents formed at the junction of the conductive surface 126 with insulative substrate 121, it also aligns electrode 120 which further contributes to the reduction of thermal spread across the tissue and a reduction of the incidence of flashover, and stray current concentrations.

In the particular representative embodiments shown in the various figures, substrate 121 is made from molded plastic material and is shaped to mechanically engage a corresponding socket 41 located in jaw member 44 of end effector 24 (see FIG. 2). The substrate 121 not only insulates the electric current but it also aligns electrode 120 both of which contribute to the reduction of thermal spread across the tissue and a reduction of the incidence of flashover. Moreover, by attaching the conductive surface 126 with insulating layer 127 to the substrate 121 utilizing one of the above assembly techniques, the alignment and thickness, i.e., height "h2", of the electrode 120 can be controlled.

Moreover, it is contemplated that an overmolding technique provides even deposition of insulation upon the insulating layer 127 disposed along the side of the electrically conductive surface. Such resulting configurations reduce stray currents, and thermal spread due to less electrode to tissue contact. It is envisioned that by dimensioning substrate, e.g., 121, insulating layer 127, and electrode 120 in this fashion (i.e., with reduced conductive surface area), the current is restricted (i.e., concentrated) to the intended area rather than stray currents developing and/or current traveling to tissue outside the intended area which may come into contact with an outer edge of the electrode 120. Additional insulation along the side of the electrically conductive surface also effectively reduces the incidence of flashover.

Substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44. A slide-fit technique is also contemplated such as the slide-fit technique described in PCT publication No. WO02080793 entitled VESSEL SEALING FORCEPS WITH DISPOSABLE ELECTRODES by Tetzlaff et al., the entire contents of which is hereby incorporated by reference herein.

Conductive surface 126 may include a wire crimp 145 designed to engage the distal end 90 of prong 105 of electrode assembly 21 and electrically engage a corresponding wire connector affixed to wire 60 located within electrode assembly 21. Conductive surface 126 also includes an opposing face 125 which is designed to conduct an electrosurgical current to a tubular vessel or tissue 150 when it is held thereagainst. It is envisioned that the conductive surfaces 126 (116) may be dimensioned as a sealing surface, a clamping surface and/or a shearing or cutting surface depending upon a particular purpose.

Referring to FIG. 5A, electrode 110 includes similar elements and materials for insulating and conducting electrosurgical current to tissue 150. More particularly, electrode 110 includes an electrically conductive surface 116, insulating layer 140, and an electrically insulative substrate 111 which are attached to one another by one of the above methods of assembly. Insulating layer 140 is disposed upon the outer edge of electrically conductive substrate 116. Insulating layer 140 is made from semi-conductive material, conductive material, insulating material, and/or combinations of these materials. Moreover, the insulating material can be the same or different from the material used to make insulating layer 127. However, it is envisioned that insulating layer 140 can and insulative layer 127 can be substantially identical, except for the placement on either electrode 120 or electrode 110.

Substrate 111 includes a plurality of detents 112 which are dimensioned to engage a corresponding plurality of sockets 43 and aperture 65 located in jaw member 42. Conductive surface 116 includes an extension 155 having a wire crimp 119 which engages the distal end 91 of prong 103 and electrically engages a corresponding wire connector affixed to wire 62 located in housing 71. Conductive surface 116 also includes an opposing face 115 which conducts an electrosurgical current to a tubular vessel or tissue 150 when it is held there against. It is contemplated that electrodes 110 and 120 can be formed as one piece and include similar components and/or dimensions for insulating and conducting electrical energy in a manner to effectively reduce thermal spread, incidence of flashover and/or stray current development. In particular, stray current may be further restricted by casting the forceps and/or manufacturing the forceps using a non-conductive material and/or coating the edges of the electrodes 110 and 120 with an insulative coating, and/or adding an insulating layer therebetween.

As mentioned above, it is envisioned that flashover, stray current concentrations, and thermal spread may be reduced by altering the physical dimensions (geometry/shape) of the insulators, or the chemical characteristics of the insulators and/or adding an insulating layer between the junction of the conductive surface and insulating substrate. With particular respect to thermal spread, it is envisioned that manufacturing the electrodes 110 and 120 in this fashion will reduce thermal spread and stray currents that may travel to the electrosurgical instrument. More particularly, the varying geometry of the insulator 111 compared to the electrically conductive surface 116 also isolates the two opposing poles during activation thereby reducing the possibility that tissue or fluids will bridge a path for stray current travel to surrounding tissue. With respect to flashover, altering the geometry of the insulator 111 and/or conductive surface creates a longer path for the current to travel over the insulator 111 before flashover occurs.

Figure 5B:
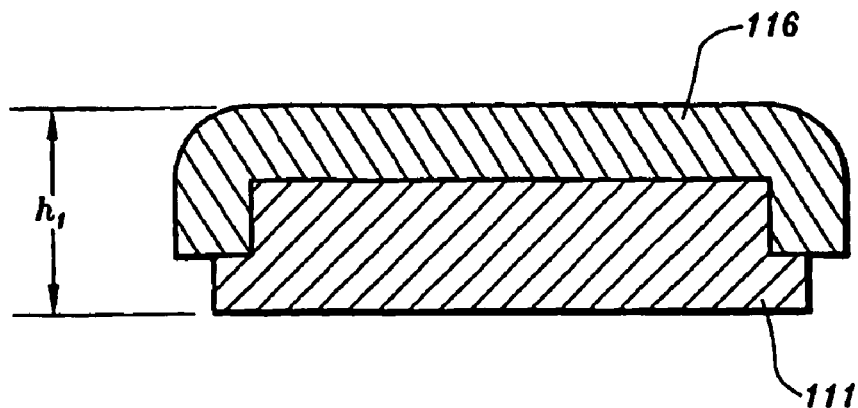
FIG. 5B is a cross section of a prior art electrode configuration with the electrode extending over the sides of the insulator.

As best shown in the comparison of FIG. 5B (prior art) with newly disclosed FIGS. 5C, 5D, 5E, 5F, 5G, 12D and 12E substrates 111, 121 are designed to extend along width "W" such that the width "W" of the insulating substrate, e.g., 111, exceeds the width "W1" of the electrically conductive surface, e.g., 116. Insulating layer 140 is disposed upon the conductive surface 116 at the junction between the conductive surface 116 and the insulating substrate 111.

Figure 5C:
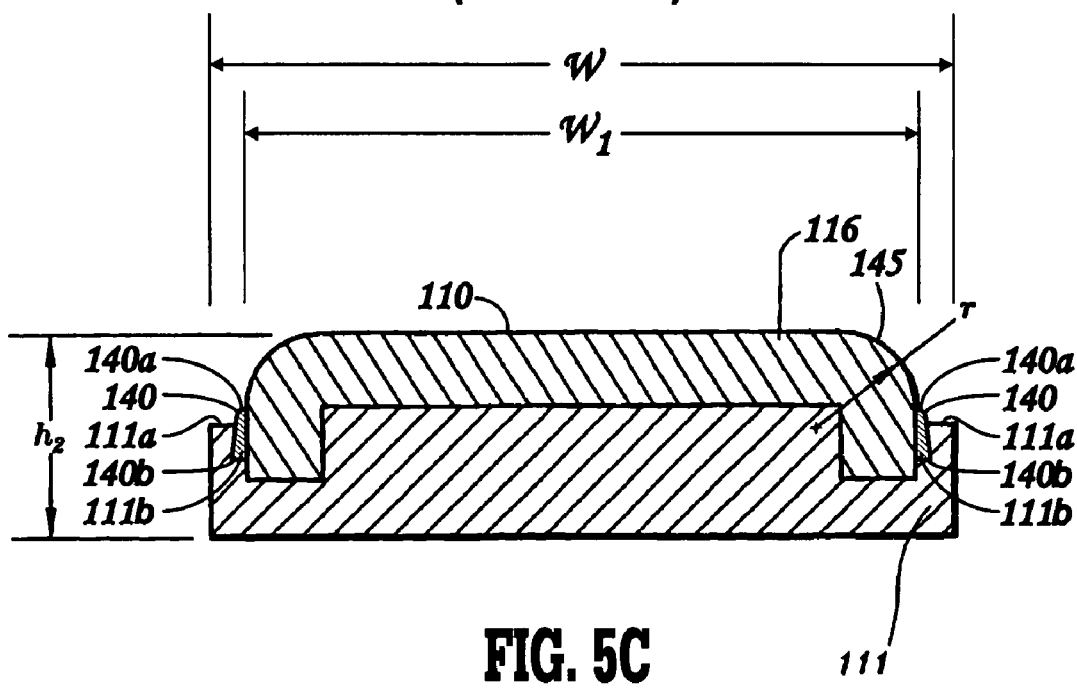
FIG. 5C is a cross section of an electrode with the insulating layer.
Figure 5D:
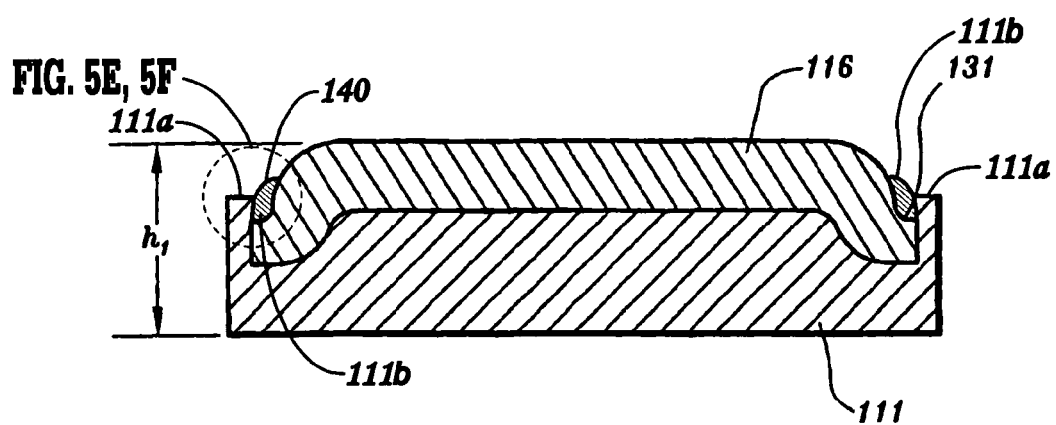
FIG. 5D is a cross section of an overmolded stamped electrode configuration showing the insulator capturing a pinch trim which depends from the electrically conductive surface having an insulating layer disposed thereon.

Referring particularly to FIG. 5C, it is envisioned that insulator substrate 111 may meet outer periphery 145 in a generally tangential fashion about radius "r". Again, this profile also tends to reduce current concentration and thermal spread and may also contribute to a reduction in the incidence of flashover. More particularly, FIG. 5C illustrates the electrode 110 of the electrode 110, 120 configuration of FIGS. 4 and 5A, respectively, wherein the pair of electrodes 110, 120 each includes an electrically conductive surface 116, 126, an insulating substrate 111, 121 having a top or first edge 111a (shown in FIG. 5C for electrode 110 only), and an insulating layer 140 positioned in a channel 111b formed by the electrically conductive surface 116 within the top or first edge 111a between the conductive surface 116 (shown in FIG. 5C for electrode 110 only) and the top or first edge 111a of the insulating substrate 111. The insulating layer 140 has a portion 140a proximal to the electrically conductive surface 116 and a portion 140b distal from the electrically conductive surface 116 and a gradient such that the proximal portion 140a has a lower dielectric strength than the distal portion 140b.

Additionally, it is envisioned that the electrically conductive surface 116 and insulating layer 140 configurations may be accomplished by various manufacturing techniques such as thermally sprayed processes, vacuum deposition processes, powder coating processes, or any other process known in the art for depositing one or more thin layers onto a surface.

Figure 5G:
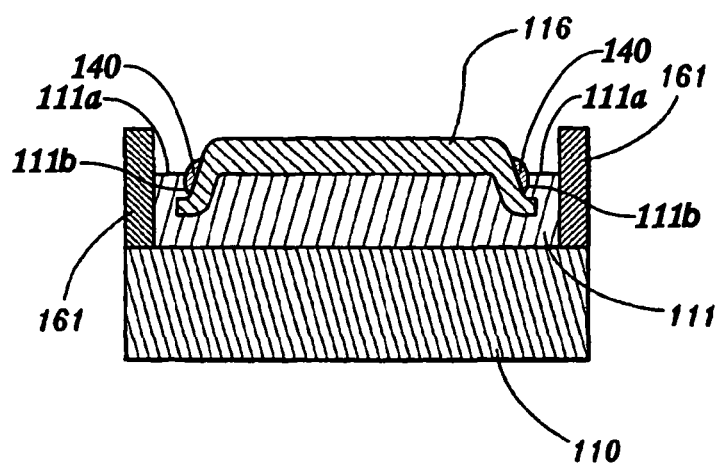
FIG. 5G is a cross section of an electrode configuration showing a compliant barrier disposed about the periphery of the electrode, insulating layer, and/or insulator.
Figure 5E:
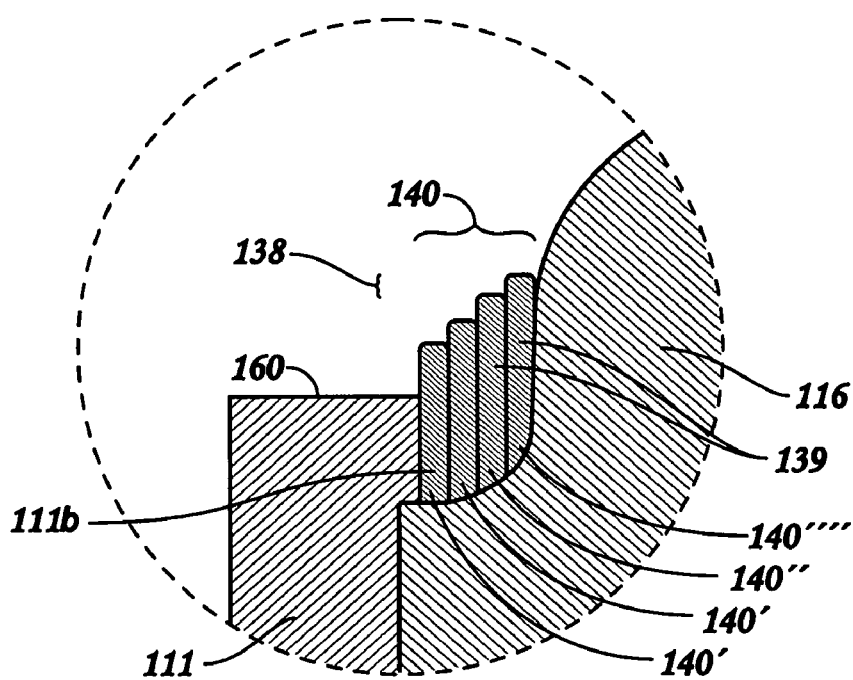
FIG. 5E is an enlarged cross section of one insulator layer suitable for use with the electrode configuration of FIG. 5D.

As best seen in FIG. 5E, a plurality of layers can be applied such that the layer adjacent to the substrate is the longest, and each subsequent layer added thereto extends away from the conductive surface 116 becomes shorter and shorter. It is envisioned that the deposition of various insulative layers, such as films, allows a dielectric gradient to form where the dielectric strength of the top portion of the insulative layer (adjacent to the conductive layer) is less than the dielectric strength of the bottom portion of the insulative layer (adjacent to the insulating substrate). For example, referring to FIG. 5E, insulative layer 140 is made of a plurality of layers 140', 140", 140''' and 140''''. Insulative layer 140'''' adjacent to the conductive surface 116 is longer than other layers, which become shorter as they are deposited further away from conductive surface 116. By providing insulative layers of various lengths, the thickness of the insulative layer 140 varies from top to bottom. It is envisioned that a gradient forms where the dielectric strength of the top portion 138 of insulative layer 140 (adjacent to the conductive layer) is less than the dielectric strength of the bottom portion 139 of the insulative layer 140 (adjacent to the top portion 160 of the insulating substrate 111).

The insulative layer 140 may be configured such that the dielectric strength of the top portion of the insulative layer is different from the dielectric strength of the bottom portion to reduce energy concentrations between the top edge 160 of the insulating substrates 111, 121 and the electrically conductive surface 116, 126. For example, referring now to FIG. 5F, an enlarged view of the junction between the conductive surface 116 and the insulating substrate 111 is shown having a different configuration than the insulating layer 140 of FIG. 5F. Here, insulating layer 240 has at least one middle portion 240″ between the top portion 238 and the bottom portion 239. The insulative layer 240 may be configured to have at least one middle portion 240″ having a higher dielectric strength than the top portion 238, and a lower dielectric strength than the bottom portion 239.

Figure 5F:
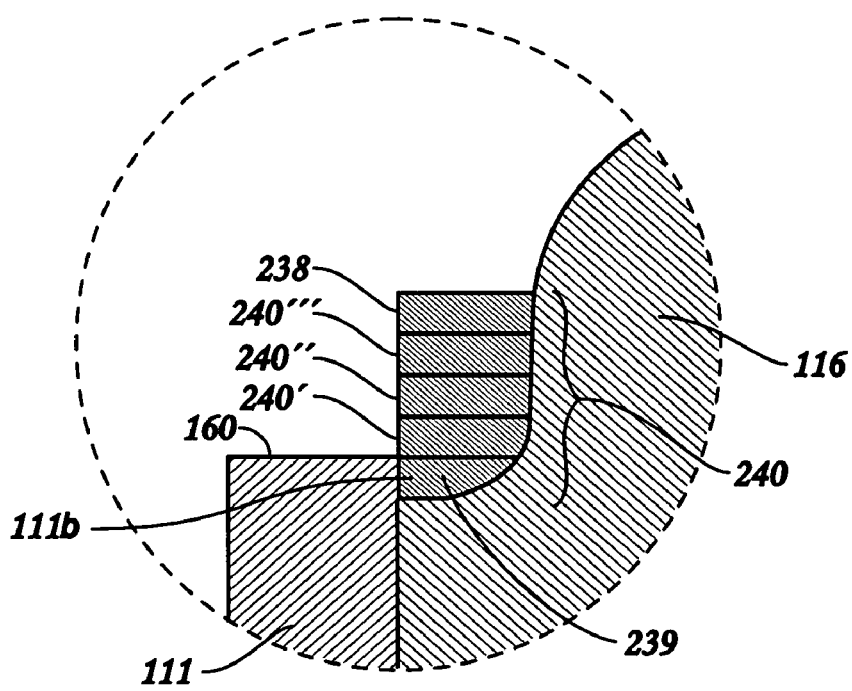
FIG. 5F is an enlarged cross section of another insulator layer suitable for use with the electrode configuration of FIG. 5D.

Still referring to FIG. 5F, a plurality of middle portions 240′, 240″, 240‴ are shown. Each middle portion 240′, 240″, and 240‴ has various dielectric strengths such that a gradient is formed. It is envisioned that by creating a dielectric strength gradient in the middle portions, the dielectric strength of the top portion 238 of the insulating layer 240 is different from the dielectric strength of the bottom portion 239 to reduce energy concentrations between the top edge of the insulating substrate 111 and the electrically conductive surface 116.

In some embodiments, the gradient is formed such that the top portion 238 of the insulating layer has a lower dielectric strength than middle portion 240‴. Middle portion 240‴ has a lower dielectric strength than middle portion 240″. Middle portion 240″ has a lower dielectric strength than middle portion 240′. Middle portion 240′ has a lower dielectric strength than bottom portion 239.

After the deposition of the insulating layer 140, the electrically conductive surface 116 and insulator 111 configurations may be accomplished by various manufacturing techniques such as overmolding of a stamping and/or metal injection molding. Stamping is defined herein to encompass virtually any press operation known in the trade, including, but not limited to: blanking, shearing, hot or cold forming, drawing, bending and coining. Other manufacturing techniques may also be employed to achieve similar electrically conductive surface 116 and insulator 111 configurations which will effectively reduce thermal spread to adjacent tissue. The electrode assembly may also include a pinch trim 131 (FIG. 5D) which facilitates secure, integral engagement of the insulate 111 and the electrically conductive surface 116 during the assembly and/or manufacturing process.

FIG. 5G shows another embodiment of the present disclosure wherein a compliant material 161 is disposed about the outer peripheries of the electrically conductive surfaces 116, 126, insulating layer 140, and the substrates 111, 121. It is envisioned that the compliant material 161 acts as a mechanical barrier by restricting heat and steam emanating from the surface thereby reducing thermal spread to surrounding tissue. One or more barriers 161 may be attached to the end effectors 22, 24 and/or the insulting substrate 111, 121 depending upon a particular purpose of to achieve a particular result.

Figure 7:
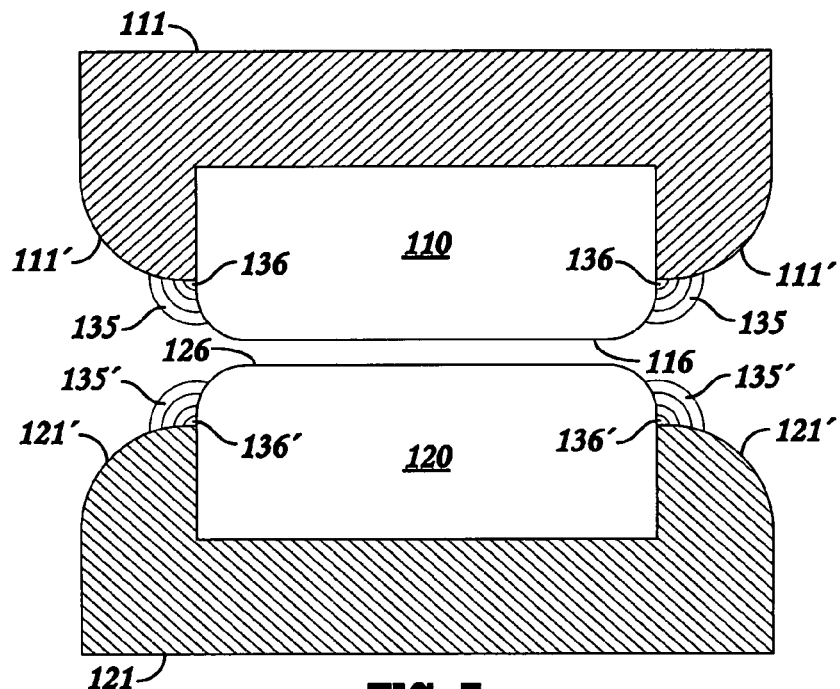
FIG. 7 is a cross-sectional view of a prior art electrode assembly illustrating current density distribution occurring in a prior art electrode assembly.
Figure 8:
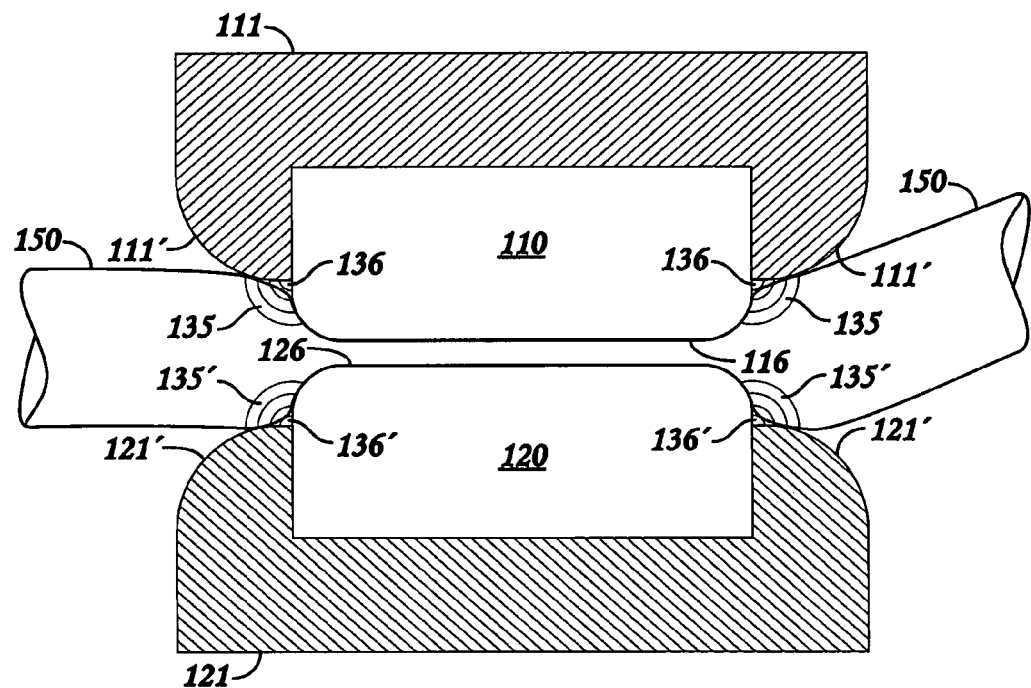
FIG. 8 is a view of the prior art electrode assembly of FIG. 7 illustrating locations where the current densities may damage to vessel tissue.

For example and by way of illustration, FIGS. 7-8 show other electrode 110, 120 configurations which are known in the prior art. FIG. 7 shows an example of opposing electrodes 110, 120 that are embedded in electrically insulating substrates 111, 121, to expose the opposing electrically conductive surfaces 116, 126, respectively. During activation, stray electrical current density distributions 135, 135′ emanate from the opposing electrically conductive surfaces 116, 126 at junction points 136, 136′ between external surfaces 111′, 121′ of electrically insulating substrates 111, 121 and the opposing electrically conductive surfaces 116, 126, respectively. As can be appreciated by referring to FIG. 8, the electrical current density distributions 135, 135′ emanate well beyond the intended treatment site and therefore can contribute to increased collateral damage to tissue of tubular vessel 150 and possible cutting thereof.

Figure 12:
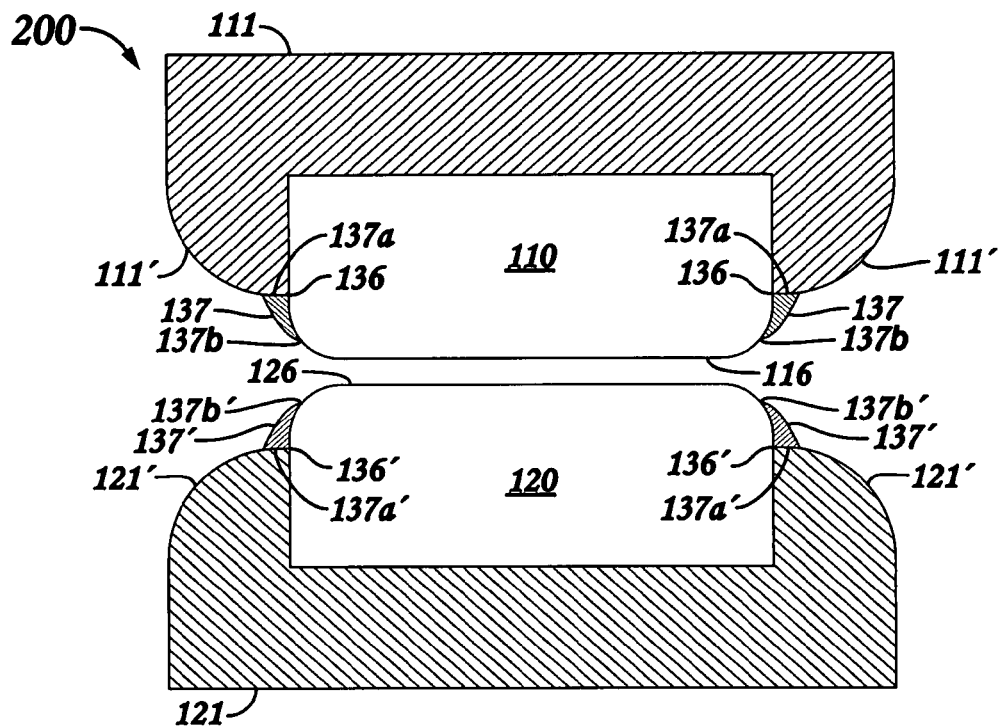
FIG. 12 is a cross-sectional view of an electrode assembly having gradient coatings according to the present disclosure.

Referring now to FIG. 12, there is illustrated an electrode assembly 200 having gradient coatings according to the present disclosure. More particularly, electrode assembly 200 includes a pair of opposing electrodes 110′ and 120′ that may be symmetrically disposed with respect to each other. Each of the opposing electrodes 110′, 120′ includes an electrically conductive surface 116, 126 and an insulating substrate 111, 121 having an exterior surface 111′, 121′, respectively. The exterior surface 111′, 121′ of the insulating substrate 111, 121 intersects the electrically conductive surface 116, 126 to form at least one insulator-conductor junction point 136, 136′ therebetween, respectively. Each of the opposing electrodes 110′, 120′ also includes a coating 137, 137′ disposed in proximity to the at least one insulator-conductor junction point 136, 136′, respectively. The coating 137, 137′ provides a dielectric gradient such that a portion 137a, 137a′ of the coating in closest proximity to the exterior surface 111′, 121′ of the insulating substrate 111, 121 has a dielectric strength that is greater than the dielectric strength of a portion 137b, 137b′ of the coating 137, 137′ in closest proximity to the electrically conductive surface 116, 126, respectively. Thus, the dielectric gradient and positioning of the coating 137, 137′ in proximity to the at least one insulator-conductor junction point 136, 136′ facilitates a reduction in current densities and in the formation of hot spots.

Figure 13:
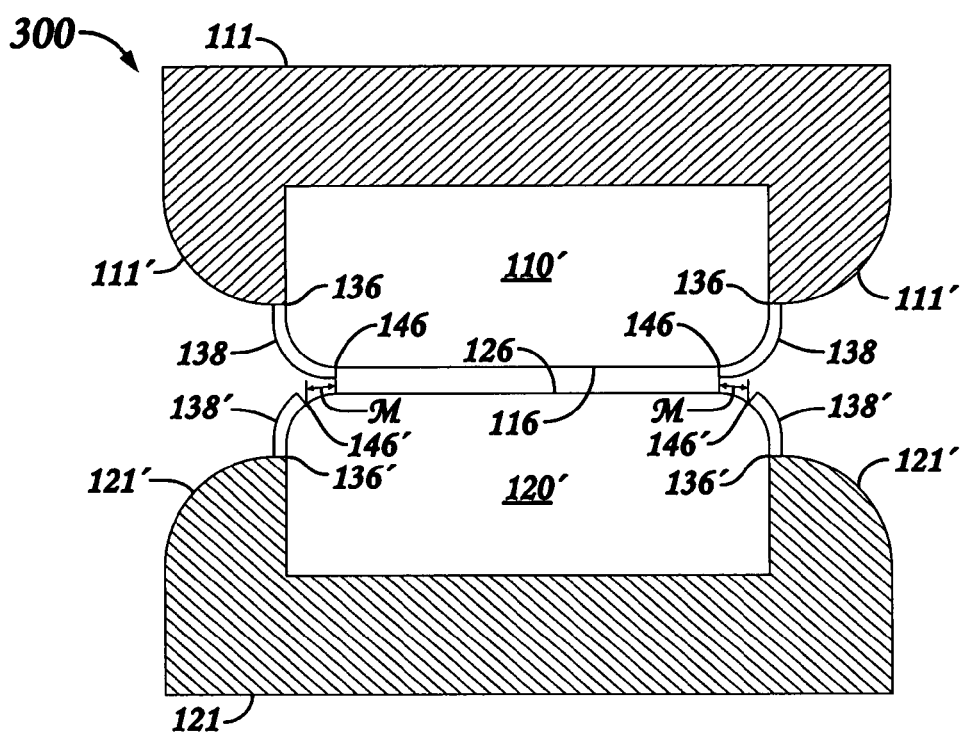
FIG. 13 is a cross-sectional view of an electrode assembly having offset coatings according to the present disclosure.

As used herein, "offset" generally refers to misaligning corresponding parts or components in relation to one another. More particularly, there is illustrated in FIG. 13 an electrode assembly 300 having misaligned or offset coatings according to the present disclosure. Again, as with respect to electrode assembly 200 illustrated in FIG. 12, opposing electrodes 110′, 120′ are embedded in electrically insulating substrates 111, 121, to expose the symmetrically opposing electrically conductive surfaces 116, 126, respectively. The pair of symmetrically disposed opposing electrodes 110′, 120′ each includes an electrically conductive surface 116, 126 and an insulating substrate 111, 121 having exterior surface 111′, 121′, respectively. The exterior surface 111′, 121′ of the insulating substrate 111, 121 again intersects the electrically conductive surface 116, 126 to form the at least one insulator-conductor junction point 136, 136′ therebetween, respectively. However, a coating 138, 138′ is now disposed in proximity to the at least one insulator-conductor junction point 136, 136′, respectively. The coating of one of the pair of electrodes extends along the electrically conductive surface so as to be misaligned with respect to the coating extending along the electrically conductive surface of the other of the pair of symmetrically disposed opposing electrodes. That is, the coating, e.g., coating 138, on one of the pair of electrodes, e.g., electrode 110′, is disposed in at least partial non-vertical registration with the coating, e.g., coating 138′, on the opposing one of the pair of electrodes, e.g., electrode 120′.

For example, coating 138 of electrode 110′ extends along the electrically conductive surface 116 to a position 146 while coating 138′ of electrode 120 extends a lesser distance along the electrically conductive surface 116 to a position 146′ such that coatings 138 and 138′ are misaligned with respect to each other. Thereby, the current densities that form at the junction points 136, 136′ are reduced in comparison to an electrode assembly wherein the coating of one electrode extends an approximately equal distance along the electrically conductive surface as the coating of the other electrode. In other words, the coating of one of the pair of electrodes extends along the electrically conductive surface so as to expose an area of the electrically conductive surface that differs from the area of the electrically conductive surface exposed by the coating extending along the electrically conductive surface of the other of the pair of electrodes.

Although it is contemplated that geometric modification of the insulator 111 relative to the electrically conductive sealing surface 116 reduces the incidence of flashover and thermal spread, in some cases, a different material may be utilized for the insulator to reduce flashover and thermal spread. For example and with particular respect to flashover, it is known that all plastics have a different resistance to flashover which is commonly measured using a Comparative Tracking Index (CTI). The CTI value required to resist flashover is typically dictated in part by the maximum voltage of the electrosurgical generator, however, other parameters such as frequency also typically have an effect on flashover.

In addition to changing the geometry of the insulator 111 and/or conductive surface 116, a plastic insulation can be employed having a CTI value of about 300 to about 600 volts. Examples of high CTI materials include nylons and syndiotactic polystryrenes such as QUESTRA® manufactured by DOW Chemical. Other materials may also be utilized either alone or in combination to reduce flashover, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenyleneoxide dispersion and Acrylonitrile Styrene Acrylate.

In some cases, however, both the geometry of the insulator 111 and/or conductive surface 116 may be altered and/or a plastic insulation may be utilized that does not have a CTI value of about 300 to about 600 volts. Alternatively, certain coatings can be utilized either alone or in combination with one of the above manufacturing techniques to reduce flashover and thermal spread.

It has also been found that offsetting or misaligning the electrodes effectively reduces: the undesirable effects of thermal spread across tissue structures; the incidence of flashover; and/or energy concentrations or heat that can occur during activation of an electrosurgical device at the junction between an insulating material and an active conductor. For example and by way of illustration, FIGS. 14A, 14B and 15 show configurations of misaligned or offset electrodes 110, 120 that are suitable for use in accordance with the present disclosure.

As previously mentioned, as used herein, "offset" generally refers to misaligning corresponding parts or components in relation to one another. For example, FIG. 7 shows an example of the opposing electrically conductive surfaces 116, 126 that are not offset. As can be appreciated, the electrically conductive surfaces 116 and 126 are aligned such that upon closure of the end effectors, the outer peripheries of electrically conductive surfaces 116, 126 come together such that the insulator-conductor junctions 136 and 136' substantially line up.

Figure 14A:
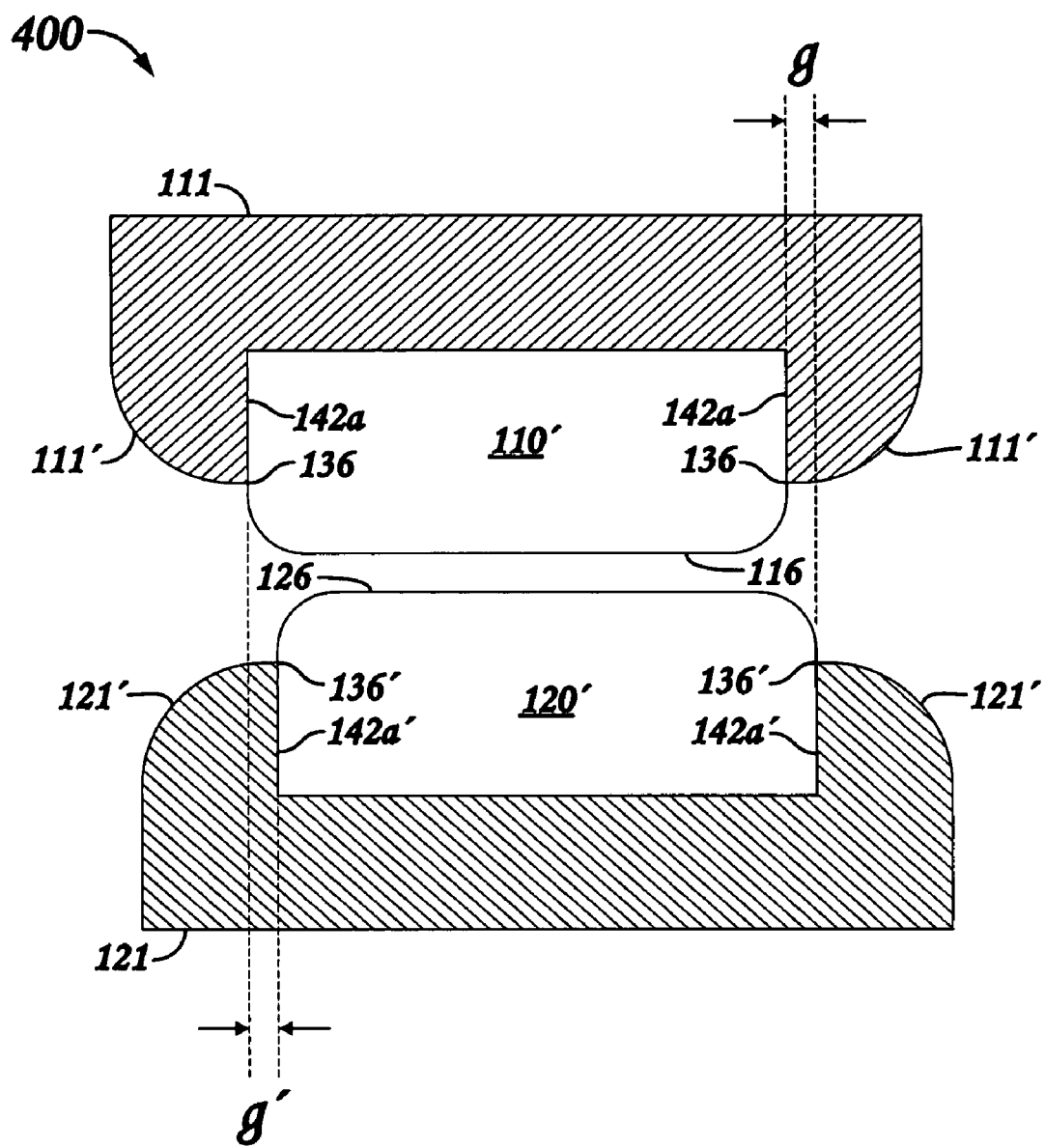
FIG. 14A is a cross-sectional view of an electrode assembly having mis-aligned or offset electrodes according to the present disclosure.
Figure 14B:
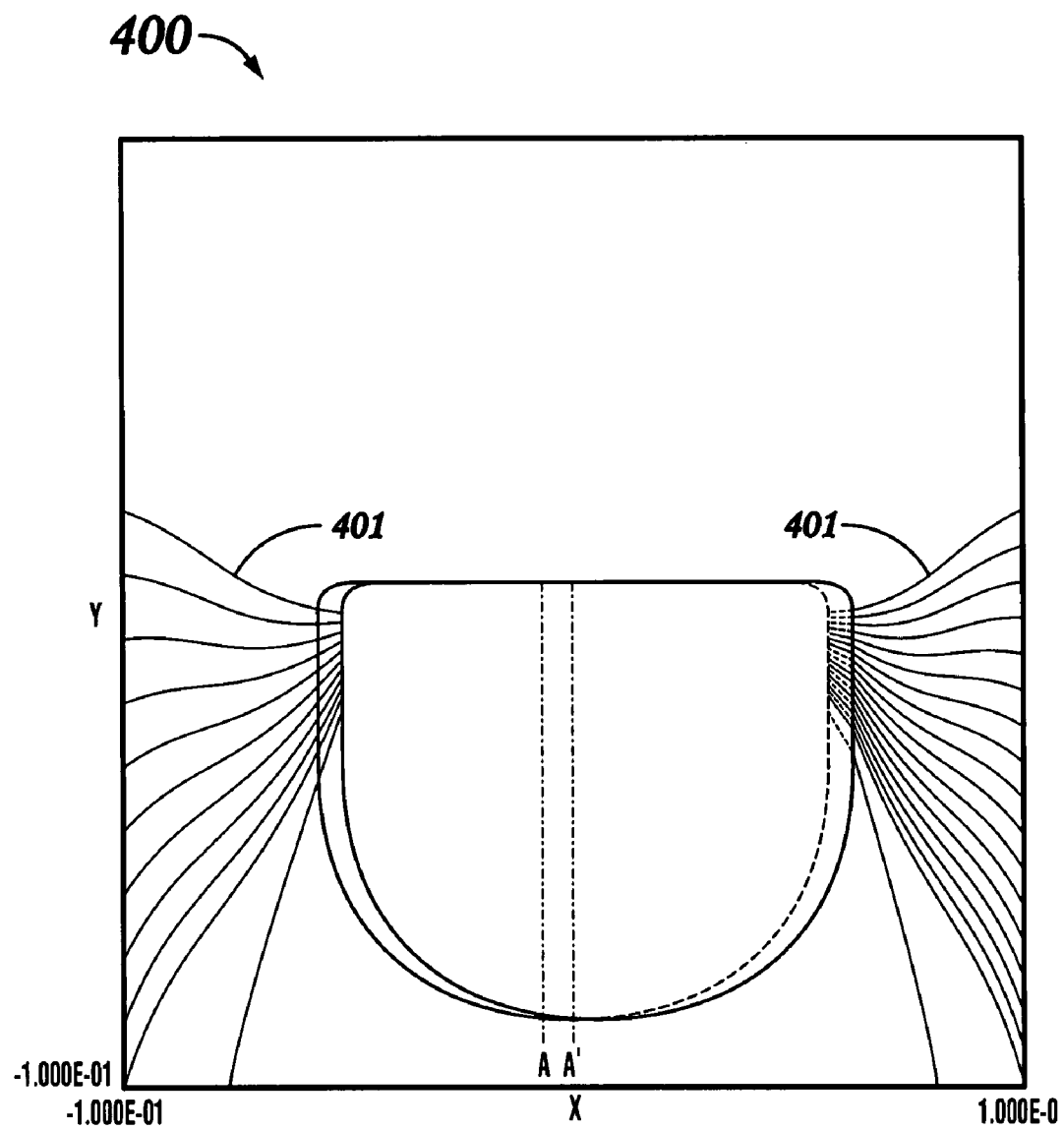
FIG. 14B a top down view of a contour plot showing dissipation of electrosurgical current across tissue using the substantially closed mis-aligned or offset electrodes of FIG. 14A.
Figure 15:
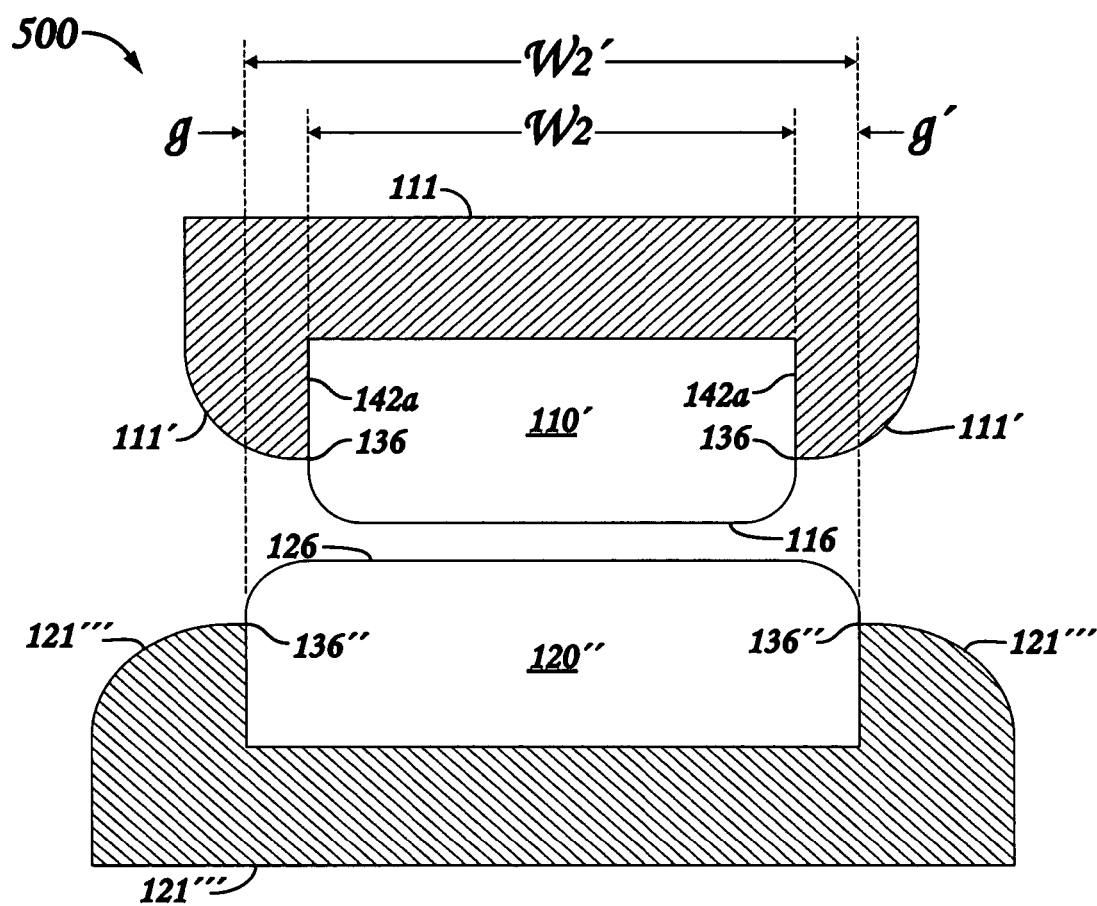
FIG. 15 is a cross-sectional view of another embodiment of the electrode assembly of FIG. 14 having mis-aligned or offset electrodes.

Referring now to FIGS. 14A and 14B, there is illustrated an electrode assembly 400 according to the present disclosure in which an electrically conductive surface of one of the pair of opposing electrodes is disposed with respect to the electrically conductive surface of the other of the pair of opposing electrodes such that at least one insulator-conductor junction of one of the pair of opposing electrodes is misaligned with respect to the insulator-conductor junction of the other one of the pair of opposing electrodes. In a similar manner as described above with respect to electrode assembly 200 (see FIG. 12), each of the opposing electrodes 110', 120' includes an electrically conductive surface 116, 126 and an insulating substrate 111, 121 having an exterior surface 111', 121', respectively. The exterior surface 111', 121' of the insulating substrate 111, 121 intersects the electrically conductive surface 116, 126 to form at least one insulator-conductor junction point 136, 136' therebetween, respectively. However, longitudinal edges 142a of electrode 110' do not substantially line up with longitudinal edges 142a' of electrode 120', and the longitudinal edges 142a' are displaced with respect to the longitudinal edges 142a by a distance "g" and are not substantially in longitudinal alignment. That is, the electrically conductive surface, e.g., conductive surface 116, of one of the pair of opposing electrodes, e.g., electrode 110', is disposed in at least partial non-vertical registration with the electrically conductive surface, e.g., conductive surface 126, on the opposing one of the pair of electrodes, e.g., electrode 120'. Thereby, the electrically conductive surface of one of the pair of opposing electrodes, e.g., surface 126 of electrode 120', is disposed with respect to the electrically conductive surface of the other of the pair of opposing electrodes, e.g., surface 116 of electrode 110', such that the at least one insulator-conductor junction of the one of the pair of opposing electrodes, e.g., insulator-conductor junction 136' of electrode 120', is misaligned, e.g., by distance "g" with respect to the at least one insulator-conductor junction of the other one of the pair of opposing electrodes, e.g., insulator-conductor junction 136 of electrode 110.

FIG. 14B illustrates that by offsetting electrodes 110', 120', current concentrations such as 401 do not overlap upon closure of the electrode assembly 400. Rather, upon closure of the electrode assembly 400, the longitudinal axis "A" lies adjacent to longitudinal axis "A'". The current concentrations 401 may be adjacent to one another respectively, upon closure of the electrode assembly 400. It is envisioned that such a configuration negates or minimizes the detrimental effects of merging current concentrations during closure, such as illustrated by electric fields 135, 135' in FIGS. 7 and 8.

Those skilled in the art will recognize that the electrode assembly 200 illustrated in FIG. 12 having gradient coatings 137, 137' may also be misaligned or offset by distance "g" in a similar manner as electrode assembly 400 described above with respect to FIGS. 14A-14B.

Referring now to FIG. 15, there is disclosed an electrode assembly 500 that is identical to the electrode assembly 400 except that with respect to the electrode assembly 500, the electrically conductive surface of one of the pair of opposing electrodes has a cross-sectional width dimension that is greater than a cross-sectional width dimension of the other of the pair of opposing electrodes. More particularly, electrode assembly 500 includes the electrode 110' having a cross-sectional width dimension "$W_2$'" between longitudinal surfaces 142a. However, electrode assembly 500 now includes an electrode 120" which has a cross-sectional width dimension "$W_2$'" between longitudinal surfaces 142a' that is greater than the cross-sectional width dimension "$W_2$'" between longitudinal surfaces 142a of electrode 110'. Correspondingly, the width of electrically insulative substrate 121" in contact with the electrode 120" is also greater than the width of the electrically insulative substrate 111 in contact with the electrode 110'. Thereby, the electrically conductive surface of one of the pair of opposing electrodes, e.g., surface 126' of electrode 120", is disposed with respect to the electrically conductive surface of the other of the pair of opposing electrodes, e.g., surface 116 of electrode 110', such that the at least one insulator-conductor junction of the one of the pair of opposing electrodes, e.g., insulator-conductor junction 136' of electrode 120", is misaligned, e.g., by distances "g, g'", with respect to the at least one insulator-conductor junction of the other one of the pair of opposing electrodes, e.g., insulator-conductor junction 136 of electrode 110'. The distances "g" and "g'" may be equal or may differ from one another.

In a similar manner as with respect to electrode assembly 400, it is envisioned that the configuration of electrode assembly 500 negates or minimizes the detrimental effects of merging current concentrations during closure, such as illustrated by electric fields 135, 135' in FIGS. 7 and 8.

Those skilled in the art will recognize that, in a manner similar to electrode assembly 200 described above with respect to FIG. 12, the electrode assembly 500 may further include the coating 137, 137' disposed in proximity to the at least one insulator-conductor junction point, e.g., insulator-conductor joints 136, 136', wherein the coating 137, 137' provides a dielectric gradient such that a portion of the coating 137, 137' in closest proximity to the exterior surface 111', 121' of the insulating substrate 111, 121" has a dielectric strength that is greater than the dielectric strength of a portion of the coating 137, 137' in closest proximity to the electrically conductive surface 116, 126', respectively.

As a result of the foregoing, FIGS. 14A, 14B and 15 illustrate an electrode assembly 400 (see FIGS. 14A-14B), or an electrode assembly 500 (see FIG. 15), of which each may include the pair of opposing electrodes 110', 120' or 110', 120", respectively. Each electrode 110', 120' or 110', 120", includes the electrically conductive surface 116, 126 and an insulating substrate 111, 121 or 111, 121" having an exterior surface 111', 121', respectively. The exterior surface 111', 121' of the insulating substrate 111, 121 or 111, 121" intersects the electrically conductive surface 116, 126 or 116, 126' to form at least one insulator-conductor junction point 136, 136' therebetween, respectively. The electrically conductive surface of one of the pair of opposing electrodes, e.g., surface 116 of electrode 110', is disposed with respect to the electrically conductive surface of the other of the pair of opposing electrodes, e.g., surface 126 of electrode 120' or surface 126' of electrode 120", such that the insulator-conductor junction of the one of the pair of opposing electrodes, e.g., insulator-conductor junction 136' of electrode 120' or of electrode 120", is misaligned or offset with respect to the insulator-conductor junction of the other of the pair of opposing electrodes, e.g., insulator-conductor junction 136 of electrode 110', respectively.

Figure 9:
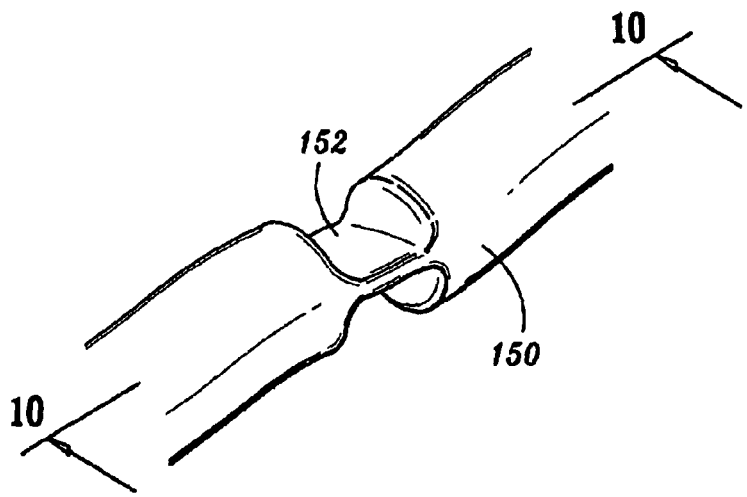
FIG. 9 is an enlarged, partial perspective view of a sealing site of a tubular vessel.
Figure 10:
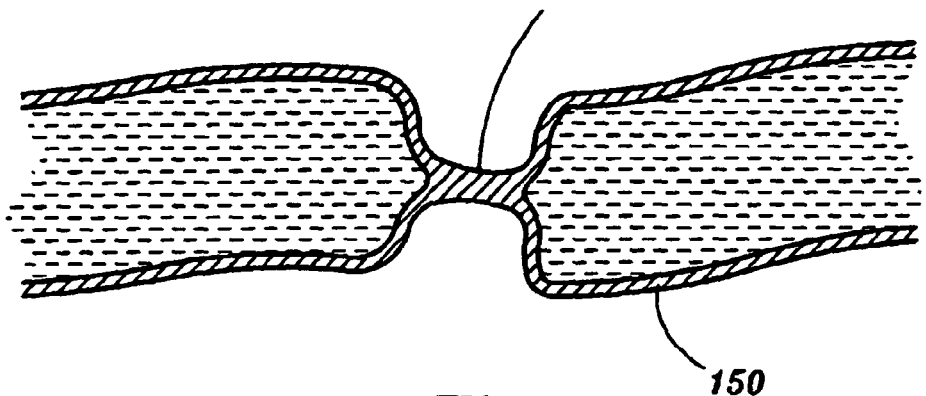
FIG. 10 is a longitudinal cross-section of the sealing site taken along line 10-10 of FIG. 9.
Figure 11:
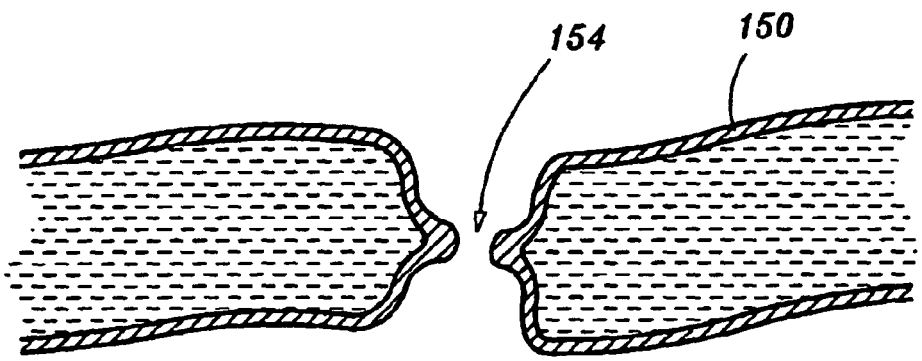
FIG. 11 is a longitudinal cross-section of the sealing site of FIG. 9 after separation of the tubular vessel.

Turning back to FIG. 6A, one embodiment of the present disclosure shows a bipolar forceps 10 during use wherein the handle members 16 and 18 are moved closer to one another to apply clamping force to the tubular tissue 150 to effect a seal 152 as shown in FIGS. 7 and 8. Once sealed, the tubular vessel 150 can be cut along seal 152 to separate the tissue 150 and form a gap 154 therebetween as shown in FIG. 9. Alternatively, the electrically conductive surfaces 116, 126, electrodes 110, 120 and/or the jaw members 42, 44 may be dimensioned as shearing surfaces which effectively cut the tissue when the jaw members 42, 44 are moved relative to one another.

After the bipolar forceps 10 is used or if the electrode assembly 21 is damaged, the electrode assembly 21 can be easily removed and/or replaced and a new electrode assembly 21 may be attached to the forceps in a similar manner as described above. It is envisioned that by making the electrode assembly 21 disposable, the electrode assembly 21 is less likely to become damaged since it is only intended for a single operation and, therefore, does not require cleaning or sterilization. As a result, the functionality and consistency of the components, e.g., the electrically conductive surfaces 126, 116, insulating layers 140, 140', and insulating surfaces 121, 111, will assure a reliable reduction of thermal spread across tissue and/or reduce the incidence of flashover, and/or minimize stray current concentrations. Alternatively, the entire electrosurgical instrument may be disposable which, again, may contribute to a reduction of thermal spread across tissue and/or reduce the incidence of flashover.

Figure 6A:
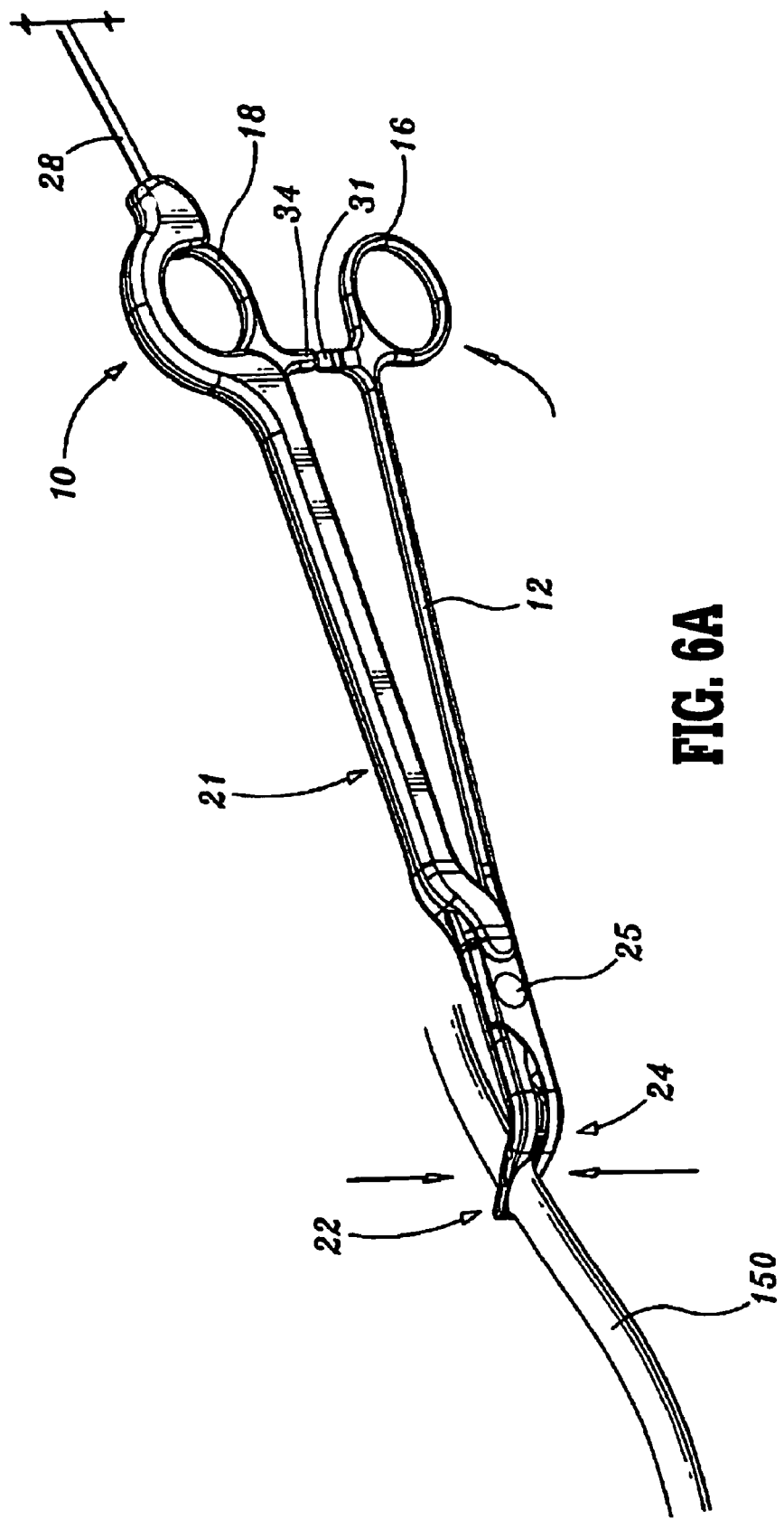
FIG. 6A is a perspective view of the open forceps of the present disclosure showing the operative motion of the electrosurgical instrument about a tubular vessel.
Figure 6B:
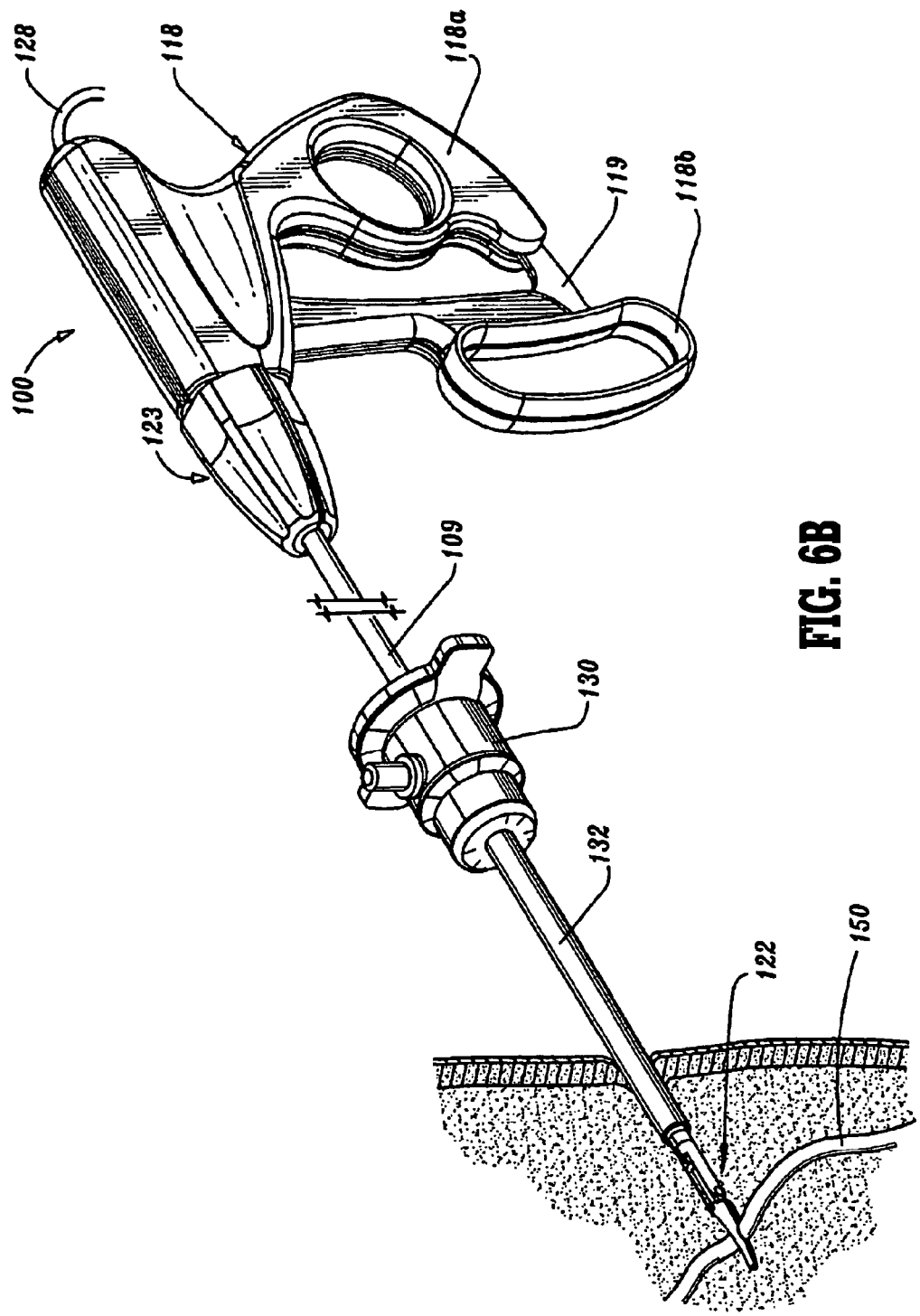
FIG. 6B is a perspective view of an endoscopic version of the present disclosure showing the operative motion of the instrument.

FIG. 6B shows an endoscopic bipolar instrument 100 during use wherein movement of a handle assembly 128 applies clamping force on the tubular tissue 150 to effect a seal 152 as shown in FIGS. 7-9. As shown, a shaft 109 and the electrode assembly 122 are inserted through a trocar 130 and cannula 132 and a handle assembly 118 is actuated to cause opposing jaw members of the electrode assembly 122 to grasp tubular vessel 150 therebetween. More particularly, a movable handle 118b is moved progressively towards a fixed handle 118a which, in turn, causes relative movement of the jaw members from an open, spaced-apart position to a closed, activation position. A rotating member 123 allows the user to rotate the electrode assembly 122 into position about the tubular tissue 150 prior to activation. Again, the electrically conductive surfaces 116, 126, electrodes 110, 120 and/or the jaw members 42, 44 may be dimensioned as shearing surfaces which effectively cut the tissue when the jaw members 42, 44 are moved relative to one another.

After the jaw members are closed about the tissue 150, the user then applies electrosurgical energy via connection 128 to the tissue 150. By controlling the intensity, frequency and duration of the electrosurgical energy applied to the tissue 150, the user can either cauterize, coagulate/desiccate, seal, cut and/or simply reduce or slow bleeding with minimal collateral or thermal damage to surrounding tissue and with minimal incidence of flashover.

From the foregoing and with reference to the various figure drawings, those skilled in the art will appreciate that certain modifications can also be made to the present disclosure without departing from the scope of the present disclosure. For example, although electrodes 110 and 120 may be configured to meet in parallel opposition, and, therefore, to meet on the same plane, in some cases, the electrodes 110 and 120 may be slightly biased to meet each other at a distal end such that additional closure force on the handles 16 and 18 is required to deflect the electrodes in the same plane.

It is envisioned that the outer surface of the end effectors may include a nickel-based material, coating, stamping, metal injection molding which is designed to reduce adhesion between the end effectors (or components thereof) with the surrounding tissue during activation.

Although the foregoing description and accompanying drawings have provided as examples of the present disclosure electrosurgical instruments and electrode assemblies that are associated with vessel sealing technology, the embodiments of the present disclosure may also be applied to other electrosurgical instruments and electrode assemblies, which include scissors, knives, pencils and ablation assemblies.

While embodiments of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical instrument having opposing end effectors and a handle for effecting movement of the end effectors relative to one another, comprising:
   a pair of electrodes each including an electrically conductive surface, an insulating substrate having a first edge, and an insulating layer positioned in a channel formed by the electrically conductive surface within the first edge between the conductive surface and the first edge of the insulating substrate, the insulating layer having a portion proximal to the electrically conductive surface and a portion distal from the electrically conductive surface and a gradient such that the proximal portion has a lower dielectric strength than the distal portion.

2. An electrosurgical instrument according to claim 1, wherein the insulating layer has varying dielectric strengths between the proximal portion and the distal portion.

3. An electrosurgical instrument according to claim 1, wherein the proximal portion is less insulating than the distal portion.

4. An electrosurgical instrument according to claim 1, wherein the insulating layer has at least one middle portion between the proximal portion and the distal portion.

5. An electrosurgical instrument according to claim 4, wherein at least one middle portion comprises a plurality of middle portions with various dielectric strengths.

6. An electrosurgical instrument according to claim 4, wherein the at least one middle portion has a higher dielectric strength than the proximal portion, and a lower dielectric strength than the distal portion.

7. An electrosurgical instrument according to claim 1, wherein the dielectric strength of the proximal portion is different from the dielectric strength of the distal portion to reduce energy concentrations between the first edge of the insulating substrate and the electrically conductive surface.

8. An electrosurgical instrument according to claim 1, wherein the insulating layer is made of material comprising ceramic, polymer, thermoplastic, semi-conductive material, and combinations thereof.

9. An electrosurgical instrument according to claim 1, wherein the insulating layer is mounted to the electrically conductive surface by a process selected from the group consisting of an overmolding process, a thermal spraying process, a vacuum deposition process, and a powder coating process.

10. An electrosurgical instrument according to claim 1 wherein the insulating layer is a semi-conductive material, conductive material, insulating material, or combinations thereof.

11. An electrosurgical instrument according to claim 10 wherein the semiconductive material comprises semiconductive polymer.

12. An electrosurgical instrument according to claim 10 wherein the conductive material comprises conductive composites, conductive polymers, metal, carbon black, and combinations thereof.

13. An electrosurgical instrument according to claim 1, wherein the electrically conductive surfaces are offset in relation to one another.

14. An electrosurgical instrument according to claim 1 wherein the electrically conductive surfaces of the opposing jaw members cooperate to seal tissue.

* * * * *